United States Patent [19]
Kunz et al.

[11] Patent Number: 5,674,714
[45] Date of Patent: Oct. 7, 1997

[54] PROCESS FOR INDUCING CYTOCHROME P-450 ENZYMES IN STREPTOMYCES BACTERIA AND DETERMINING THE MUTAGENICITY OF CHEMICALS

[75] Inventors: Daniel Anthony Kunz, Denton, Tex.; Sima Fateme Sariaslani, Newark, Del.

[73] Assignee: E. I. Du Pont de Nemours and Company, Wilmington, Del.

[21] Appl. No.: 976,034

[22] Filed: Nov. 13, 1992

Related U.S. Application Data

[62] Division of Ser. No. 751,046, Aug. 28, 1991, Pat. No. 5,213,971, which is a division of Ser. No. 207,630, Jun. 16, 1988, Pat. No. 5,169,755, which is a continuation-in-part of Ser. No. 947,669, Dec. 30, 1986, abandoned.

[51] Int. Cl.$^6$ .............................. C12Q 1/00; C12N 9/00; C12N 15/53; C12N 15/76
[52] U.S. Cl. .................. 435/71.2; 424/94.4; 435/5; 435/7.4; 435/29; 435/189; 435/252.1; 435/252.35; 435/886; 435/897
[58] Field of Search ..................... 424/94.4; 435/71.2, 435/886, 897, 5, 189, 29, 7.4, 244, 252.1, 252.35

[56] References Cited

FOREIGN PATENT DOCUMENTS

| 213898 | 3/1987 | European Pat. Off. . |
| 243856 | 11/1987 | European Pat. Off. . |
| 258899 | 3/1988 | European Pat. Off. . |
| 273771 | 7/1988 | European Pat. Off. . |

OTHER PUBLICATIONS

Romesser et al, Biochem, Biophys Res Commun. 140 650–659 (1986).
Batzinger, et al. Cancer Research. 38. 608–612 1978.
Chem Abstacts. Abstract No. 908765. 1985 v. 102 n. 11.
König WA, et al. Helvetica Chimica Acta v. 60 Fasc. 6 (1977) p. 2071.
Chem Abstracts. Abstract No. 92763 p. 92762 vol. 105. 1986.
Chem Abstracts. Abstract No. 116872y p. 173 vol. 96. 1982.
Chem abstracts. Abstact No. 192830p p. 142 vol 98. 1938.
F. Sariaslani et al., *Biochem. Biophys. Res. Commun.* 170(2):456 (1990).
F. Sariaslani et al., *Biochem. Biophys. Res. Commun.* 166(2):743 (1990).
F. S. Sariaslani, *Adv. Applied. Microbiol.* 36:133 (1991).
Shoun, et al., *J. Biochem.*, 94:1219–1229 (1983).
Shoun, et al., *J. Biochem.*, 97 755–763 (1985).
Sutherland, *Appl. Environ. Microbiol.*, 52:98–100 (1986).
Callen, et al., *Mutation Research*, 45:309–324 (1977).
McCoy, et al., *Mutation Research*, 46(4):261–264 (1977).
Romesser, et al., *Biochem. Biophys. Res. Commun.*, 140:650–659 (1986).
Wikke, et al., "Soyprotein and Human Nutrition", 209–233 (Academic Press) NY 1979.
Paradi, et al., *Mutation Research* 20:283–294 (1988).
Chem Ab., vol. 106, No. 7, Abstract No. 47028n (16 Feb. 1987).
F. S. Sariaslani, et al., "Induction of Cytochrome P–450 in *Streptomyces griseus* by Soybean Flour," *Biochem. Biophys. Res. Commun.*, 141(2):405–410 (1986).

*Primary Examiner*—Michael G. Wityshyn
*Assistant Examiner*—Jane Williams

[57] ABSTRACT

A process for inducing cytochrome P-450 enzyme production in bacteria of the genus Streptomyces using inducers such as soybean flour, genistein or genistin is described. Uses for the cytochrome P-450 enzymes produced are also discussed as is a process for using genetically engineered Streptomyces to determine the mutagenicity of chemicals.

2 Claims, 2 Drawing Sheets

5,674,714

PROCESS FOR INDUCING CYTOCHROME P-450 ENZYMES IN STREPTOMYCES BACTERIA AND DETERMINING THE MUTAGENICITY OF CHEMICALS

RELATED APPLICATION

This is a division of application Ser. No. 07/751,046, filed Aug. 28, 1991, now U.S. Pat. No. 5,213,971, which is a division of application Ser. No. 07/207,630 filed Jun. 16, 1988, now U.S. Pat. No. 5,169,755, which is a continuation-in-part of U.S. Ser. No. 06/947,669, filed Dec. 30, 1986, now abandoned.

BACKGROUND OF THE INVENTION

1. Field of the Invention

This invention relates to a process for inducing cytochrome P-450 enzyme production in bacteria of the genus Streptomyces using inducers such as soybean flour, genistein or genistin. Streptomyces enriched in their cytochrome P-450 concentration are useful in carrying out a number of important chemical conversions including the conversion of procarcinogens into mutagens. This invention also relates to a process for determining the mutagenicity of a chemical, using novel bacterial organisms containing both the means to activate promutagens and the means to detect the mutagenic activity of mutagens.

2. Background

Cytochrome P-450 is a term for a group of unique heme proteins which form carbon monoxide complexes with a major absorption band at wavelengths around 450 nm. These proteins are isozymes which carry out oxidase functions in a wide variety of mixed function oxidase systems involved in biosynthesis and catabolism of specific cell or body components, and in the metabolism of foreign substances entering organisms. Oxygenating enzymes such as P-450 appear to be fundamental cellular constituents in most forms of aerobic organisms. The activation of molecular oxygen and incorporation of one of its atoms into organic compounds catalyzed by these enzymes are reactions of vital importance not only for biosynthesis and degradation of steroid hormones necessary for sustaining life, but also for metabolic activation or inactivation of foreign agents such as drugs, food preservatives and additives, insecticides, carcinogens and environmental pollutants.

It is an object of the present invention to provide a process for the production of cytochrome P-450 enzymes which utilizes bacteria from the genus Streptomyces and a soybean derivative such as soybean flour, or the isoflavonoids genistin or genistein. One of the surprising aspects of the invention is that the Streptomyces cytochrome P-450 enzymes are induced, not by a known substrate, but by certain soybean derivatives. It is also an object of the present invention to provide bacteria enriched in cytochrome P-450 which are useful in carrying out mutagenicity assays. The P-450 enzymes in such enriched bacteria bear a resemblance, in their oxidative reactions, to the cytochrome P-450 enzymes of mammalian liver and thus may serve as an economical and convenient source of cytochrome P-450 for use in a modified version of an Ames-type Salmonella assay for carcinogenicity and mutagenicity. Although cytochrome P-450 isozymes are found in a wide variety of organisms and tissues, they vary greatly in their composition and functions they can perform. Thus, it is suprising that the cytochrome P-450 enzymes of Streptomyces carry out a spectrum of oxidative reactions that are sufficiently similar to those carried out by the cytochrome P-450 enzymes of the mammalian liver that they may serve as a substitute in the Ames test.

It is a further object of the present invention to develop a process to detect the mutagenic activity of chemicals using novel, genetically engineered Streptomyces organisms and a single incubation of said organisms with suspected carcinogenic chemicals, thus greatly simplifying the screening of chemicals for mutagenic activity. Furthermore, the process of this invention obviates the use of mammalian liver extracts for the conversion of promutagens to mutagens. These and other objects and advantages of the present invention will become apparent hereinafter.

SUMMARY OF THE INVENTION

The present invention contemplates a process for inducing cytochrome P-450 enzyme production in bacteria from the genus Streptomyces comprising culturing the bacteria in a culture medium comprising at least one inducer selected from the group consisting of soybean flour, Bactosoytone™, and soypeptone™, genistein and genistin. The invention also relates to products produced by this process.

In addition, the invention contemplates a method for evaluating the potential mutagenic activity of a substance which comprises the consecutive steps of: (a) culturing cytochrome P-450 induced bacteria from the genus Streptomyces in a culture medium comprising the substance to be evaluated; (b) incubating an amino acid requiring mutant strain of *Salmonella typhimurium* in the presence of a sample of the bacterial culture from (a); and (c) determining the number of resulting amino acid sufficient revertant colonies.

Furthermore, the invention contemplates a method for evaluating the mutagenic activity of a substance which comprises the consecutive steps of: (a) culturing cytochrome P-450 induced genetically engineered bacteria from the genus Streptomyces in a culture medium comprising the substance to be evaluated and (b) determining whether or not there is a significant increase in the reversion rate of a mutation-dependent marker of the bacteria.

BRIEF DESCRIPTION OF THE DRAWINGS

FIG. 1(A) represents the FPLC analysis of a 35–45% pellet fraction and FIG. 1(B) represents the FPLC analysis of a 45–55% pellet fraction.

DETAILED DESCRIPTION OF THE INVENTION

Figure 1A:
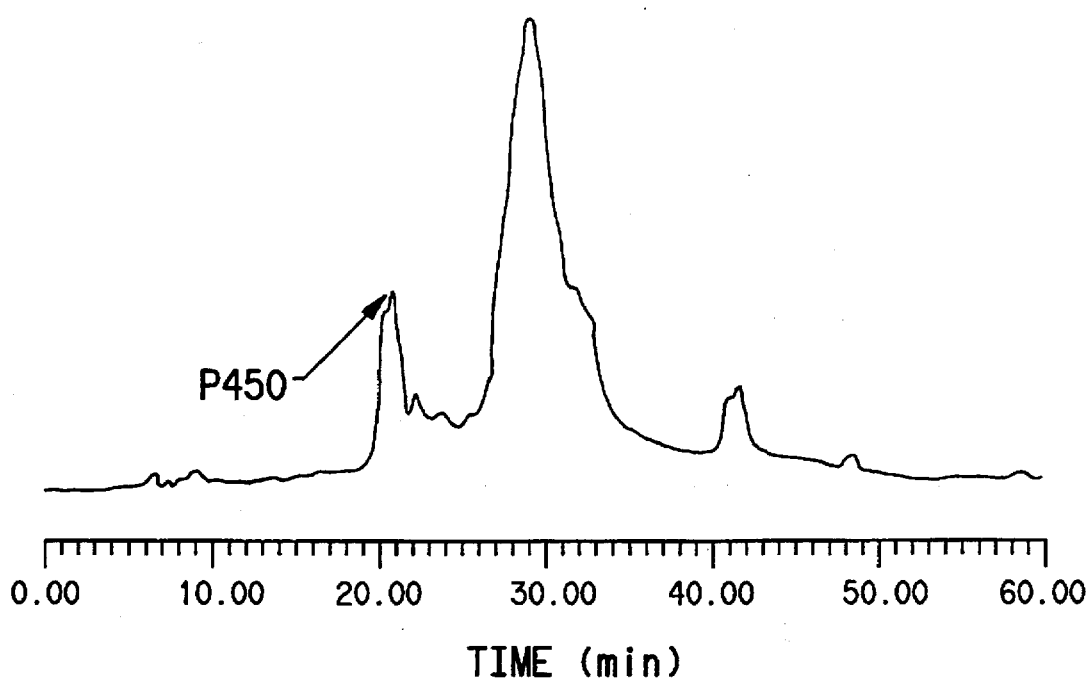
FIGS. 1(A) and (1B) illustrate the FPLC profiles of ammonium sulfate pellets of *S. griseus* extracts grown on soybean medium, as described in Example 26.

The process of the invention is carried out by culturing bacteria of the genus Stretomyces in a culture medium containing a cytochrome P-450 inducer. Suitable bacteria include, but are not limited to, *Streptomyces griseus* ATCC No. 13273, *Streptomyces griseus* ATCC No. 10137, *Streptomyces griseus* ATCC No. 13968, *Streptomyces griseus* ATCC No. 21897, *Streptomyces griseus* NRRL No. B-8090, (ATCC No. 55185 ) deposited Mar. 20, 1975 *Streptomyces punipalus* NRRL No. 3529 and *Streptomyces griseolus* ATCC No. 11796, and combinations thereof. Preferably the bacteria utilized are selected from the group consisting of *Streptomyces griseus* ATCC No. 13273, *Streptomyces griseus* ATCC No. 10137, *Streptomyces griseus* ATCC No. 13968, *Streptomyces griseus* NRRL No. B-8090, *Streptomyces punipalus* NRRL No. 3529 and *Streptomyces griseo-*

*lus* ATCC No. 11796. More preferably, the bacteria are selected from the group consisting of *Streptomyces griseus* ATCC No. 13273 deposited May 11, 1988, *Streptomyces griseus* ATCC No. 10137, deposited Oct. 28 1946, *Streptomyces griseus* NRRL No. B-8090. Most preferably, the bacteria are *Streptomyces griseus* ATCC No. 13273. As used herein, the designation "ATCC" refers to the American Tissue Culture Collection depository located in Rockville, Md. The "ATCC No." is the accession number to cultures on deposit at the ATCC. As used herein, the designation "NRRL" refers to the U.S. Department of Agriculture, Northern Regional Research Laboratories, located in Peoria, Ill., and the "NRRL No." is the accession number to cultures on deposit at the NRRL. In addition, Streptomyces bacteria suitable for use in the present induction process are also found in most soils and can be isolated therefrom using conventional methods which are apparent to those skilled in the art.

Contemplated inducers include soybean derivatives such as soybean flour, Bacto-soytone™, soypeptone™, genistein, genistin, and combinations thereof. Preferably, the inducer is soybean flour, Bacto-soytone™, soypeptone™ or genistein. More preferably, the inducer is soybean flour or genistein. Most preferably, from an activity standpoint, the inducer is genistein. As used herein, soybean flour includes both finely ground soybean powder and coarsely ground soybean meal. Preferably, the soybean flour is a finely ground powder. Soybean flour is commercially available from Natural Sales Co., P.O. Box 25, Pittsburgh, Pa. 15230 and Sigma Chemical Co., P.O. Box 14508, St. Louis, Mo. 63178. Bacto-soytone™ can be obtained from Difco Labs, Detroit Mich., 28232 and Soypeptone™ from Sigma Chemical Co. Genistein is available from K&K Labs, Plainview, N.Y. 11803. Soybean flour, genistein and genistin can each be obtained from soybeans using conventional methods which are apparent to those skilled in the art.

As will be clear to those skilled in the art, the amount of inducer required will vary depending upon the inducer utilized, the bacterial species and strain employed, the particular nutrient medium used, and the extent of P-450 production desired. In general terms, the higher the concentration of inducer, the greater the amount of cytochrome P-450 enzyme produced. Relatively speaking, high levels of cytochrome P-450 enzymes can be induced using about 2.5 to 25 g/L of soybean flour, Bacto-soytone™ or Soypeptone™, or about 50 to 150 mg/L of genistin or genistein.

The culturing can be carried out in any liquid culture medium suitable for the growth of bacteria of the genus Streptomyces. Such media are well known in the art. Generally, the medium should contain, glycerol, glucose, yeast extract or soybean flour, and have a pH of about 5 to 8, with the optimum pH falling near 7.0. Preferably the medium contains soybean flour or glycerol. Most preferably, the medium contains soybean flour. Suitable buffer salts include potassium or sodium phosphate or potassium or sodium chloride.

Examples of suitable media include the following: (1) Soybean-glycerol medium: glycerol (20 g/L), yeast extract (5 g/L), NaCl (5 g/L), $K_2HPO_4$ (5 g/L) and distilled water, with the pH adjusted to 7.0 using 5N HCl ; (2) Sporulation broth: [ATCC, No. 5] yeast extract (1.0 g/L), beef extract (1.0 g/L), tryptose (2.0 g/n), $FeSO_4$ (trace), glucose (10 g/L) and distilled water, with the pH adjusted to 7.2 using 1N NaOH; and (3) Nutrient broth: bacto beef extract (3 g/L), bacto peptone (5 g/L) and distilled water; (4) M7 agar: (for spore generation); glucose (10 g/L), casein hydrolysate [N-Z amine] (2 g/L), yeast extract (1 g/L), agar (22 g/L) and distilled water, adjust to pH 7.0 with potassium hydroxide. Antibiotics are added from concentrated sterile stock solutions to sterile liquified medium which has been cooled to approximately 50° C. Suitable antibiotic concentrations are well known to those skilled in the art, and include but are not limited to 10 µg thiostrepton (Ts) per ml of medium (resulting in M7Ts plates) or 50 µg kanamycin per ml of liquid medium (resulting in M7Km plates); (5) R2YE Medium : (for regeneration of protoplasts); sucrose (103 g/L), yeast extract (5 g/L), $K_2SO_4$ (250 mg/L), $MgCl_2$-$6H_2O$ (10.1 g/L), glucose (10 g/L), casamino acids (100 mg/L), $KH_2PO_4$ (50 mg/L), $CaCl_2$-$2H_2O$ (295 mg/L), proline (300 mg/L), TES buffer (573 mg/L), NaCl (292 mg/L), $ZnCl_2$ (trace), $FeCl_3$-$6H_2O$ (trace), $CuCl_2$-$2H_2O$ (trace), $MnCl_2$-$4H_2O$ (trace), $Na_2B_4O_7$-$1H_2O$ (trace), $(NH_4)6Mo_7O_{24}$-$4H_2O$ (trace), agar (22 g/L) and distilled water. Soft R2YE agar is made by substituting agar at 7 g/L for agar at 22 g/L; (6) S-medium: (for protoplast formation); peptone (5 g/L), yeast extract (5.1 g/L), $KH_2PO_4$ (2.5 g/L), $K_2HPO_4$ (5 g/L), glucose (1 g/L), $MgSO_4$-$7H_2O$ (500 mg/L), glycine (525 mg/L); and (7) 1/2YEME: yeast extract (3 g/L), peptone (5 g/L), malt extract (3 g/L), glucose (1 g/L), sucrose (170 g/L), $MgCl_2$-$6H_2O$ (1 g/L). Other suitable media are described in Koenig et al., Helv. Chim. Acta, 60: 2071–8 (1977). Another solution of importance is Protoplasting buffer: sucrose (103 g/L), $K_2SO_4$ (250 mg/L), $MgCl_2$-$6H_2O$ (2.02 g/L), $CaCl_2$-$2H_2O$ (368 mg/L), TES buffer (573 mg/L), $ZnCl_2$ (trace), $FeCl_3$-$6H_2O$ (trace), $CuCl_2$-$2H_2O$ (trace), $MnCl_2$-$4H_2O$ (trace), $Na_2B_4O_7$-$1H_2O$ (trace), $(NH_4)6Mo_7O_{24}$-$4H_2O$ (trace) and distilled water.

Generally, the cultures should be maintained at temperatures between about 20°–37° C., preferably between about 25°–37° C., with the optimum growth temperature at about 28°–30° C.

A suitable culturing procedure requires growing the bacteria in a suitable culture medium containing one or more of the inducers for up to about 5 days at a temperature between about 25° and 37° C., and transferring the bacteria into a fresh inducer-containing medium maintained within the same temperature range. The bacteria are then maintained in the fresh medium for up to about 5 days. The period of growth prior to a transfer into fresh inducer-containing medium is termed "stage 1", and the organisms from this period of growth are called "first stage" organisms. The growth period after the transfer of organisms from the first stage into new inducer-containing medium is termed "stage 2" and the organisms from this stage called "second stage" organisms. This culturing procedure is termed a two-stage culturing protocol. The most preferred culturing procedure is carried out by growing the bacteria in stage 1 at 28°–30° C. for 3 days, transferring the bacteria to fresh medium and growing in stage 2 for one additional day at the same temperatures. Preferably the cultures in stages 1 and 2 are incubated with shaking.

The bacteria can then be harvested from the bacterial culture by centrifugation. Centrifugation rates of 8,000–15,000×g for 15–30 minutes can be employed to yield a cellular pellet portion and a substantially cell-free supernatant. Preferably, a rate of 9,000×g for 20 minutes is used.

Cytochrome P-450 induced Streptomyces bacteria may be employed to determine the mutagenicity of a given substance, and the present invention also encompasses this. As used herein, mutagenicity is defined as including both mutagenicity and carcinogenicity. Specifically, the present invention contemplates two methods for for evaluating the potential mutagenic activity of a substance. Method A comprises: (a) culturing cytochrome P-450 induced bacteria from the genus Streptomyces in a culture medium comprising the substance to be evaluated; (b) incubating an amino acid requiring mutant strain of *Salmonella typhimurium* in the presence of a sample of the bacteria culture from (a); and (c) determining the number of resulting amino acid sufficient revertant colonies.

Preferably, the induced bacteria utilized in the mutagenicity assay are produced using the two-stage culturing protocol, and step (a) of the mutagenicity assay is carried out by adding the substance to be evaluated directly to the second stage culture medium containing the induced bacteria, as described in Example 38 below. Most preferably, the substance to be evaluated is added to the second stage culture medium at about 24 hr, as described in Examples 39–46 below. Other suitable variations within the ambit of the invention as described in step (a) will be apparent to one skilled in the art.

The preferred method, Method B, for evaluating the potential mutagenic activity of a substance comprises: (a) culturing cytochrome P-450 induced genetically engineered bacteria from the genus Streptomyces in a culture medium comprising the substance to be evaluated; (b) determining whether or not there is a significant increase in the reversion rate of a mutation-dependent marker gene in the genetically engineered Streptomyces.

Cytochrome P-450 induced Streptomyces bacteria for the mutagenicity assay may be obtained using the induction procedures described in detail above. The culture conditions such as culture medium, temperature, pH, etc. utilized in the induction process described herein are also suitable for carrying out step (a) of the mutagenicity assay.

The genetically engineered bacteria utilized in Method B can be made as follows: Plasmid pIJ702-Km$^r$ was produced by cloning the kanamycin resistance gene into pIJ702 and is the starting plasmid for all the subsequent plasmids constructed. Plasmid pIJ702 is described by Hopwood et al., in Genetic Manipulation of Streptomyces: a laboratory manual, John Innes Foundation, Norwich, England (1985). pIJ702-Km$^r$ is deposited in the American Type Culture Collection depository located in Rockville, Md. 20852 and bears accession number ATCC 67696. The deposit was made on May 11, 1988 under conditions complying with Section 1.207 (b) of the Budapest Treaty. Plasmid pIJ702-Km$^r$ is approximately 7.1 Kb in size and is capable of stable replication in Streptomyces and confers thiostrepton resistance and kanamycin resistance to Streptomyces. While pIJ702 and the kanamycin gene were chosen for purposes of the examples in this specification, the invention should not be limited to them. Any plasmid that replicates stably in Streptomyces is suitable. Several examples are: pSLP124, pSLP181, pIJ61, pIJ303, pIJ355, pIJ364, pIJ385. Other suitable plasmids are described by Hopwood et al., in Genetic Manipulation of Streptomyces: a laboratory manual, John Innes Foundation, Norwich, England (1985). Also while the gene for kanamycin resistance was used for purposes of example in the present specification, other selective marker genes such as tetracycline, chloramphenicol, rifampicin (rifampin), erythromycin, neomycin, hygromycin and viomycin may be used. Stocks of pIJ702-Km$^r$ are obtained by methods well known to those skilled in the art.

To obtain plasmids for testing the mutagenic capability of chemicals, mutations were produced in the selective marker genes for kanamycin resistance and thiostrepton resistance. Mutations with revertant frequencies less than $1 \times 10^{-4}$ are required. Mutations in the kanamycin and thiostrepton gene were produced by the following procedure which is a modification of the method described by Gerhardt et al., in the Manual of Methods for General Bacteriology, American Society of Microbiology, washington, D.C. (1981). Mix and sterilize: 1) Buffer A (0.4 mL) consisting of 0.5M KH$_2$PO$_4$ solution adjusted to pH 6.0 with 0.5M K$_2$HPO$_4$. Add EDTA solution to 5 mM. 2) sterile water (0.5 mL), 3) Buffer B (0.8 mL) consisting of 560 µL of 4M NaOH, 0.35 g hydroxylamine HCl, 4.0 mL water. Adjust to pH 6.0 (with either HCl or NaOH) and bring to 5.0 mL total volume with sterile distilled water. (Make Buffer B fresh each time) 4) Solution C (0.1 mL) consisting of 200 mM MgSO$_4$. Adjust several aliquots of pIJ702-Km$^r$ to contain 0.1 to 1.0 µg of DNA and adjust the volume to 200 µL of sterile TE. TE is described in Maniatis et al., Molecular Cloning, A Laboratory Manual, Cold Spring Harbor Laboratory, Cold Spring Harbor, N.Y. To each plasmid DNA solution, add 200 µL of the hydroxylamine mixture. Incubate the resulting mixtures at 37° C. for 16 hours. Remove a 250 µL aliquot from one of the samples immediately and every 2 hours and add the removed aliquot to 250 µL of a solution of sterile TE, then add 50 µL of sodium acetate solution (3M, pH 5.2), and 500 µL of isopropanol. Store at 4° C.

An additional plasmid, pFS, bearing a kanamycin resistant gene altered to kanamycin sensitivity by the insertion of an extra nucleotide base, guanine, between reading frame bases 4 and 5 to create a frameshift mutation, was also selected for use in Method B for testing the mutagenicity of chemicals. pFS is deposited in the American Type Culture Collection depository located in Rockville, Md. 20852 and bears accession number ATCC 67967. The deposit was made on May 11, 1988 under conditions complying with Section 1.207 (b) of the Budapest Treaty.

As will be clear to those skilled in the art, the method for introducing a marker gene into recipient bacteria will vary based on the nature of the DNA containing the marker gene and the bacteria into which the DNA is introduced. For purposes of this invention, only plasmids which carry a selectable marker genus and which are capable of stably replicating in the genus. Streptomyces are used.

Two methods for the generation of protoplasts which allow efficient introduction of plasmid DNA into *S. griseus* ATCC 13273 have been developed.

Method #1 is based on the method of Hopwood et al., in Genetic Manipulation of Streptomyces: a laboratory manual, John Innes Foundation, Norwich, England (1985).

Method #1 follows:
1. Add approximately $5 \times 10^5$ spores of *S. griseus* ATCC 13273 to a 125 ml flask containing 25 ml of ½ YEME medium and incubate at 28° C. while shaking at 125 RPM for 24 hours.
2. Subculture the resulting culture of 1 by adding 2 ml from it to a 125 ml flask containing 25 ml of S-medium and incubate at 28° C. while shaking at 125 RPM for 24 hours.
3. Centrifuge the culture resulting from 2 in a superspeed centrifuge at 700×g for 10 minutes at 4° C. Decant the supernatant and resuspend the pellet in 15 ml of 10.3% aqueous sucrose.
4. Repeat the centrifugation of step 3.
5. Resuspend the pellet in 4 ml of a 1 mg/ml solution of lysozyme, and incubate at 30° C. for 30 minutes. Triturate 3 times with the piper and reincubate at 30° C. for 15 minutes.
6. Add 5 ml of Protoplasting buffer, triturate 3 times with the pipet and filter through sterile cotton. Collect the filtrate and filter it through a filter with pores size of 5 microns.
7. Collect the filtrate of step 6 and centrifuge it in a superspeed centrifuge at 700×g for 10 minutes at 4° C. Decant and resuspend the pellet in 10 mL of protoplasting buffer.

8. Repeat the centrifugation of 7 and resuspend the resulting pellet of protoplasts in 50 ul of protoplasting buffer.

Method #2 for generating protoplasts for transformation follows:

Cultures for protoplast formation are conveniently started from spores. When started from bits of mycelium ("propagules"), the cultures grow in the form of tight nodules, and later only the cells at their surface are converted to protoplasts, resulting in low yields. On the other hand, young cultures started from spores and grown overnight in broth on a shaker, are usually well dispersed. Spores are difficult to suspend because of their hygrophobicity, but the use of wetting agents to prepare suspensions for inoculation is not reccommended. Cultures produced by normal inoculation with a loop are adequate for most purposes. Dispersion may be helped by fast rotary shaking and the use of baffled flasks, but this is not strictly necessary.

The liquid medium used is Trypticase-soy (TS) broth (described in Hopwood et al.,in Genetic Manipulation of Streptomyces: a laboratory manual, John Innes Foundation, Norwich, England (1985)) with 0.5% glycine. The amino acid can be added to the medium before autoclaving, but it is preferably added from a concentrated solution which has been filter sterilized. The concentration of the stock solution can be as high as 20%, but glycine tends to crystallize after a drop in temperature. A 10% solution can be kept in the refrigerator.

Normally, small cultures of 10 ml each in 50 ml Erlenmeyer flasks are grown. The yield from one or two such cultures is sufficient for a transformation experiment, but if one plans to preserve protoplasts in the freezer, larger volumes of cultures should be prepared.

A noticeable difference in growth yield is observed between medium containing 0.4% glycine and that containing 0.5% glycine (weaker growth at higher concentration). However, susceptibility to lysozyme becomes higher at 0.5%, and the cell yield is good enough for routine experiments.

The culture is centrifuged to collect the cells. The resulting pellet of cells is washed once with filter-sterilized sucrose (0.3–0.5M), and suspended in sterile modified P-3 medium containing 1–1.5 mg lysozyme per mL. Use of the lower concentration is preferred; protoplast formation is faster with 1.5 mg lysozyme per mL, but excess of the enzyme usually results in lower viability of the protoplasts.

The modified P-3 medium has the following composition (taken from the paper by Shirahama et al., Agr. Biol. Chem. 45: 1271–1273, (1981)):

| NaCl | 70 mM |
| MgCl$_2$ | 5 mM |
| CaCl$_2$ | 10 mM |
| sucrose | 0.5 M |
| TES buffer, pH 7.2 | 25 mM |

This differs from the original formulation in the CaCl$_2$ concentration (original: 5 nM). A 10 mM concentration seems better to preserve protoplast viability.

In the modified P-3 medium, at room temperature (20°–22° C.), and with a lysozyme concentration of 1 mg/mL, abundant protoplast formation reaching almost all cells in the population, should occur before 20 minutes.

Resulting protoplasts are suspended and released from networks of filamentous cells by gentle pipetting up and down with a Pasteur pipette. The rests of the filamentous cells can be filtered off by passing the suspension through sterile cotton or glass wool. When the original cultures are started from vegetative cells (rather than spores), there is a higher proportion of the population that resists the action of lysozyme. This is due to the fact that the population in this case is composed of cells of different ages, and normally the resistance to lysozyme increases with age.

The protoplasts are washed by sedimenting them in a bench top centrifuge. Any common clinical centrifuge can be used at a speed to provide 700 to 1000×g, centrifuging for 5 to 10 minutes. After their sedimentation, the protoplasts are washed once with PWP or modified P-3. The composition of PWP is the following:

| NaCl | 70 mM |
| MgCl$_2$ | 10 mM |
| CaCl$_2$ | 20 mM |
| sucrose | 0.5 M |
| TES, 7.2 | 25 mM |

The protoplasts are finally resuspended in P-3. Cell concentrations can be determined by counting cells in a Petroff-Hauser chamber or a common haemocytometer. Final suspensions containing $10^9$ to $10^{10}$ protoplasts per mL are best for normal operations and for preservation. The suspensions can be kept frozen at −20° C. or, better at −70° C. or in liquid nitrogen. As mentioned in Hopwood's manual (Hopwood et al.,in Genetic Manipulation of Streptomyces: a laboratory manual, John Innes Foundation, Norwich, England (1985)) (p. 13), freezing should be gradual and thawing fast. One way of having slow freezing is to put the vials in the freezer in a plastic beaker with crushed ice.

Transforming protoplasts is done by the method of Hopwood et al., supra (1985), and is briefly outlined below.

(1) Thaw protoplasts by submersing them under warm (about 37° C.) tap water.

(2) Divide the thawed suspension into aliquots with each containing approximately 5×10$^9$ protoplasts, centrifuge each aliquot at 700×g for 7 minutes at room temperature and resuspend the pellets of protoplasts in about 50 ul water with 20% glycerol.

(3) Add DNA (20 ug–200 ug) in a volume of 20 ul or less to the concentrated protoplast slurry.

(4) Immediately add 500 ul of 25% polyethylene glycol 1000 (dissolved in Protoplasting buffer) and mix once using the same pipette.

(5) As soon as possible (no longer than three minutes after adding the polyethylene glycol) add 5 ml of Protoplasting buffer and centrifuge at 700×g for 10 minutes at room temperature.

(6) Pour off the supernatant and resuspend the resulting pellet in 1 ml of Protoplasting buffer.

(7) Place 100–200 ul of transformed protoplasts on a dried R2YE agar plate and then overlay with 5 ml R2YE soft agar. Incubate at 30° C.

After 24 hours, overlay the transformed protoplasts with 5 ml R2YE soft agar containing the appropriate antibiotic (10 μg/mL of thiostrepton if selecting for thiostrepton resistance and kanamycin sensitivity, or 50 μg/mL of kanamycin if selecting for kanamycin resistance and thiostrepton sensitivity.

Twelve kanamycin-sensitive (thiostrepton resistant) derivatives of pIJ702-Km$^r$ were isolated after in vitro hydroxylamine mutagenesis of pIJ702-Km$^r$, transformation of S. griseus ATCC13273 and selection by thiostrepton, and screening for sensitivity to kanamycin. The sensitive plasmids were designated H and numbers from 60 to 71 (i.e., H60, H61, etc. to H71). The revertant frequencies of each was determined and 7 (H61, H63, H65, H66, H67, H69 and H70) of the 12 were found to exhibit potentially useful revertant frequencies (i.e., less than $1\times10^{-4}$).

Additionally, a thiostrepton-sensitive (kanamycin resistant) derivative of pIJ702-Km$^r$ was isolated after in vitro hydroxylamine mutagenesis of pIJ702-Km$^r$, transformation of *S. griseus* ATCC 13273 and selection with kanamycin. A thiostrepton sensitive plasmid was designated HTS1 and was found to exhibit a potentially useful revertant frequency.

All hydroxylamine-generated plasmids selected were approximately 7.1 Kb in size. The description of three particularly useful plasmids for determining the mutagenicity of chemicals by the preferred Method B follows:

Plasmid pH69. Made by in vitro hydroxylamine mutation of pIJ702-Km$^r$, the plasmid confers resistance to thiostrepton and contains a revertable inactive kanamycin resistance gene. The point of the mutation(s) in the kanamycin resistance gene sequence is not known. Plasmid pH69 confers a revertant rate of $2.9\times10^{-7}$ to *S. griseus* ATCC13273, and is most easily reverted by (pro)mutagens known to cause point mutations.

Plasmid pHTS1. Made by in vitro hydroxylamine mutation of pIJ702-Km$^r$, the plasmid confers resistance to kanamycin and contains a revertable inactive thiostrepton resistance gene. The point of the mutation(s) in the thiostrepton resistance gene sequence is not known. Plasmid pHTS1 confers a revertant frequency of $1.7\times10^{-8}$ to *S. griseus* ATCC 13273, and is most easily reverted by (pro)mutagens known to cause point mutations.

Plasmid pFS. Plasmid pFS contains a nucleotide base, guanine, inserted between reading frame bases 4 and 5 to create a frameshift mutation. Plasmid pFS confers a rate of reversion to kanamycin resistance of $9.8\times10^{-7}$ to *S. griseus* ATCC 13273, and is most easily reverted by (pro)mutagens known to cause frameshift mutations.

Plasmids pH69, and pFS utilize the kanamycin resistance gene as the inactivated antibiotic resistance gene, whereas plasmid pHTS1 utilizes the thiostrepton resistance gene.

The genus and strain of the induced Streptomyces bacteria employed in step (a) of either Method A or Method B are not critical. Suitable induced Streptomyces bacteria include, but are not limited to, induced *Streptomyces griseus* ATCC No. 13273, induced *Streptomyces griseus* ATCC No. 10137, induced *Streptomyces griseus* ATCC No. 13968, induced *Streptomyces griseus* ATCC No. 21897, induced *Streptomyces griseus* NRRL No. B-8090, induced *Streptomyces griseus* NRRL No. 3529 and induced *Streptomyces griseus* ATCC No. 11796. Preferably, the induced Streptomyces bacteria employed are selected from the group consisting of induced *Streptomyces griseus* ATCC No. 13273, induced *Streptomyces griseus* ATCC No. 10137, induced *Streptomyces griseus* ATCC No. 13968, induced *Streptomyces griseus* NRRL No. B-8090, induced *Streptomyces punipulus* NRRL NO. 3529 and induced *Streptomyces griseolus* ATCC No. 11796. More preferably, the induced Streptomyces bacteria are selected from the group consisting of induced *Streptomyces griseus* ATCC No. 13273, induced *Streptomyces griseus* ATCC No. 10137 and induced *Streptomyces griseus* NRRL No. B-8090. Most preferably, the induced Streptomyces bacteria are induced *Streptomyces griseus* ATCC No. 13273.

The bacterial culture sample utilized in step (b) of Method A may be obtained by taking a sample directly from the bacterial culture in step (a). Alternatively, the bacterial culture in (a) may be centrifuged to obtain a cellular pellet portion and a substantially cell-free supernatant portion, and either portion used as the bacterial culture sample in step (b). Suitable centrifugation rates include 8,000 to 15,000×g for 15 to 30 minutes. Preferably, the centrifugation rate is 9,000×g for 20 minutes.

Incubation conditions suitable for step (b) of Method A of the mutagenicity assay will be apparent to one skilled in the art, and are described in Maron et al., Mutation Research, 113:178–179 (1983), and in Examples 38–46 below. In this regard reference may also be made to Ames et al., Proc. Natl. Acad. Sci., 70:2281 (1973); Ames et al., Mutation Research, 31:347 (1975); McCann et al., Proc. Natl. Acad. Sci. USA, 72:5135 (1975); and McCann et al., Proc. Natl. Acad. Sci. USA, 73:950 (1976).

Any amino acid requiring mutant strain of *Salmonella typhimurium* suitable for use in the well-known Ames mutagenicity assays may be employed in the present Method A mutagenicity assay. Preferably the amino acid requiring mutant strain of *Salmonella typhimurium* is a histidine requiring mutant strain. Such Salmonella are discussed, for example, in Maron et al., Mutation Research, 113:178–179 (1983), which describes a revised Ames assay. Suitable histidine requiring mutant strains include, but are not limited to strains TA 97, TA 97A, TA 98, TA 100, TA 100FR, TA 102, TA 104, TA 1535, TA 1537, TA 1538 and M 677. Preferably, the mutant strain of *Salmonella typhimurium* is selected from the group consisting of strains TA 98, TA 1535, TA 1537 and TA 1538. Most preferred, the mutant strain of *Salmonella typhimurium* is selected from the group consisting of strains TA 1535, TA 1537 and TA 1538. On deposit with the ATCC and bearing the following ATCC accession are the following strains of histidine requiring *Salmonella typhimurium*: *Salmonella typhimurium*, strain TA 1535, ATCC No. 29629; *Salmonella typhimurium*, strain TA 1537, ATCC No. 29630; and *Salmonella typhimurium*, strain TA 1538, ATCC No. 29631. On deposit with the NRRL and bearing the following NRRL accession numbers are the following strains of histidine requiring *Salmonella typhimurium*: *Salmonella typhimurium*, strain TA 98, NRRL No. B-4279; *Salmonella typhimurium*, strain TA 100, NRRL No. B-4280; *Salmonella typhimurium*, strain TA 1535, NRRL No. B-4211; *Salmonella typhimurium*, strain TA 1537, NRRL No. B-4213; and *Salmonella typhimurium*, strain TA 1538, B-4214. A number of these and other mutant strains of *Salmonella typhimurium* are also available upon request from Bruce Ames, Biochemistry Department, University of California, Berkeley, Calif. 94720. In addition, these and other mutant strains suitable for use in the present mutagenicity assay may be constructed using recombinant DNA techniques well-known to those skilled in the art.

The number of resulting amino acid sufficient revertant colonies in step (c) can be determined using techniques well-known to those skilled in the art.

In addition, cytochrome P-450 induced Streptomyces bacteria may be utilized in carrying out many commercially important oxidation reactions, as will be recognized by those skilled in the art.

The compounds which may be oxidized by the cytochrome P-450 induced Streptomyces bacteria (and the oxidized compound resulting therefrom) include the following: 7-ethoxycoumarin (7-hydroxycoumarin); precocene II (precocene-diol); anisole (phenol, 2-OH anisole); benzene (phenol); biphenyl (4-OH biphenyl); chlorobenzene (2-OH chlorobenzene); coumarin (7-OH coumarin); naphthalene (1-OH naphthalene); trans-stilbene (4-OH stilbene, 4,4'-di-OH stilbene); toluene (2-OH toluene); glaucine (predicentrine, norglaucine); 10,11-dimethoxyaporphine (apocodeine, isoapocodeine); papaverine (6-desmethylpapaverine, 7-desmethylpapaverine, 4'-desmethylpapaverine); d-tetrandrine (N'-nortetrandrine); thalicarpine (hernandalinol); bruceantin (side chain alcohols, epoxide); vindoline (dihydrovindoline ether, dihydrovindoline ether dimer, dihydrovindoline ether enamine); dihydrovindoline (11-desmethyldihydro-vindoline); leurosine (12'-hydroxyleurosine); and codeins (14-hydroxycodeine).

The preferred process of this invention for testing chemicals for mutagenicity is Method B which follows:

*Streptomyces griseus* containing the appropriate plasmid and its selective marker gene are grown by streaking a culture of said cells onto M7 agar plates and incubating the plates for several days at 25°–35° C. Spore formation is evident by the white granular appearance of the colonies. Spores are collected as described by Hopwood et al., Genetic Manipultion of Streptomyces: a laboratory manual, John Innes Foundation, Norwich, England (1985) which is as follows:

Add 9 mL of sterile water to the culture plate. Scrape the surface of the culture with a sterile inoculating loop, first with gentle pressure and gradually more vigorously, so as to suspend the spores. Pour the crude suspension into a disposable capped test tube and agitate the liquid vigorously on a vortex mixer for a minute or so. Filter the suspension through non-absorbent cotton wool, using a filter tube. Pour the filtered suspension into a centrifuge tube and centrifuge for 5–10 minutes at 700×g to pellet the spores. As soon as the centrifuge stops, pour off the supernatant. Agitate the tube on a vortex mixer for a few seconds to disperse the pellet in the drop of water remaining in the tube. Add 1–2 mL of sterile 20% glycerol and briefly agitate again. Freeze the resulting spores at −80° C. until needed for use.

To prepare cultures for testing chemicals suspected of being mutagenic, inoculate approximately 50 µl (approximately $5\times10^7$ spores) of a frozen spores stock of a strain of transformed *Streptomyces griseus* (transformed with one of the selective marker-containing plasmids) into a 125 mL flask containing 25 mL of soybean-glycerol medium. Inoculate a flask with each transformed Streptomyces to be used in the test. Add thiostrepton to each flask to a concentration of 10 µg/mL. Incubate with shaking at 125 RPM, at 28° C. for 48 to 72 hours. Cultures resulting are called Stage 1 cultures. Subculture 2 mL from each flask into two fresh 125 mL flasks, again containing 25 mL of soybean-glycerol medium and thiostrepton at a concentration of 10 µg/mL. Incubate with shaking at 125 RPM (or any speed which allows aeration and growth of the culture), at 28° C. (temperature can be 25 to 35° C.) for 24 hours. The resulting cultures are called stage 2 cultures.

Dissolve 1 to 10 mg of the suspected mutagenic or promutagenic chemical in 300 to 5000 µL of solvent. The solvent may be acetone, DMSO, toluene or a mixture of the three. Use of 1500 µL of DMSO is preferred. Add the dissolved suspected mutagenic chemical to one flask of each different transformed Streptomyces stage 2 culture in the test so that the chemical is present in a concentration between 1 and 10 mg per flask in preferably 1500 µL of DMSO. Add an equivalent amount of solvent to the duplicate flask of each different transformed Streptomyces stage 2 culture to serve as the solvent control. Incubate all the cultures with shaking at 125 RPM, at 28° C. for 3 to 24 hours in a fume hood.

Remove 1 mL aliquots from each flask and wash the cells three times with 50 mM sodium phosphate buffer (pH 7.0) or 100 mM potassium phosphate buffer (pH 6.7) to remove chemicals and media. After the third wash resuspend the washed cells of each in phosphate buffer to a total volume of 0.2 to 1.0 mL. From each suspension, remove and add 0.1 mL onto each of 1 to 10 M7-thiostrepton plates per culture. Spread cultures by streaking plates. Incubate plates for 3 days at 28° C.

Collect spores from each plate and combine the spores of plates started from the same culture. Titer each spore sample on both M7-kanamycin (M7Km) and M7-thiostrepton (M7Ts) plates. Incubate plates at 28° C. for 4 to 5 days. For each culture, determine the titer (colony forming units per milliliter) from both M7-thiostrepton and M7-kanamycin plates. Divide the titer from the M7-kanamycin plates by the titer from the M7-thiostrepton plates to determine the revertant frequency for each culture. Divide the revertant frequency for a culture treated with a chemical by the revertant frequency for the same culture not treated by a chemical to determine the mutagenic ratio. A mutagenic ratio of 1.9 or greater is statistically significant and indicates mutagenic activity by the tested chemical. A mutagenic ratio of less than 1.0 indicates toxicity of the chemical towards the bacterial strain at the concentration of the chemical used.

The invention is further described in the Examples set forth below. All experiments were conducted in accordance with the following General Methods, except where otherwise indicated. In the General Methods and Examples, all parts and percentages are by weight, and all degrees are Celsius unless otherwise noted.

General Methods

Chemicals

The soybean flour routinely used in these studies was purchased from Natural Sales Co., P.O. Box 25, Pittsburgh, Pa. 15230. Soybean flour may also be obtained from Sigma Chemical Co., P.O. Box 14508, St. Louis, Mo. 63178.

Genistein was purchased from K&K Labs., Plainview, N.Y. 11803.

Soy oil was purchased from Sigma Chemical Co., P.O. Box 14508, St. Louis, Mo. 63178.

Coumestrol was purchased from Eastman Kodak Co., Rochester, N.Y. 14650.

Daidzein was purchased from Spectrum Chemical MFG Corp., 14422 S. San Pedro St., Gardena, Calif. 90248.

Mutagens

For puposes of the examples below which utilized genetically engineered *S. griseus* strains, several known mutagenic and promutagenic chemicals where the type of mutagenic activity is known were chosen. They are (with their known method of causing mutations): N-methyl-N'-nitro-N-nitrosoguanidine (NTG),a direct-acting chemical which causes point mutations; benzo(a)pyrene (BZP), a promutagen which causes point mutations; ICR-191 (ICR191), a direct acting chemical which causes frameshift mutations; 2-aminoanthracene (2-AA), a promutagen which causes frameshift mutations.

Bacterial Strains

*Streptomyces griseus* (ATCC 13273, ATCC 10137, ATCC 13968, ATCC 21897, NRRL B-8090, ATCC 23336 and NRRL 3242).

*Streptomyces punipalus* (NRRL 3529).

*Streptomyces griseolus* (ATCC 11796).

*Streptomyces lincolnensis* (ATCC 25466).

Culture Maintenance

Bacteria were maintained on sporulation agar stock slants or plates and stored in sealed screw-capped tubes at 4°.

Media and Growth Conditions

The bacteria were grown on three different complex media. "Medium A" contains soybean flour (5 g), glycerol (20 g), yeast extract (5 g), NaCl (5 g), $K_2HPO_4$ (5 g), and distilled water (1.0 l); with the pH adjusted to 7.0 with 5N HCl. "Medium B" is sporulation broth (ATCC No. 5) and consists of yeast extract (1.0 g), beef extract (1.0 g), tryptose (2.0 g), $FeSO_4$ (trace), glucose (10 g) and distilled water (1.0 L); with the pH adjusted to 7.2 using 1N NaOH. "Medium C" is nutrient broth. Nutrient broth consists of bacto beef extract (3 g) and bacto peptone (5 g) in 1.0 L of distilled water. All media were sterilized by autoclaving.

The bacteria were grown according to a two stage fermentation protocol as described by R. E. Betts et al., J. Med. Chem. 17:599–602, (1974). Bacteria were transferred from stock slants or plates to either 25 mL or 200 mL of the relevant media and incubated with shaking (2500 rpm) at 28°–30° for three days (stage 1). A portion of the stage 1 cultures sufficient to constitute 10–20% of the volume of the new culture was used to start stage 2 cultures. Stage 2 cultures were usually incubated with shaking for 24–72 hours, preferably 24 hours.

Preparation of Cell Suspensions and Cell Extracts

Bacteria grown on liquid medium were harvested by centrifugation (9,000×g, 20 min) and washed once with one volume of buffer (pH 7.4) containing 100 mM sodium phosphate, 1 mM dithiothreitol (DTT) and 0.1 mM ethylene diaminetetraacetic acid (EDTA). This buffer is called DEP buffer. Cell suspensions in DEP buffer were prepared by suspending 5–8 g (wet weight) of centrifuged bacteria in 15–24 mL of buffer. The bacteria were disrupted by two passages through a French Pressure cell at $8.27 \times 10^6$ Pa (1200 psi) pressure. The resulting viscous liquids (19–29 mL) were digested with deoxyribonuclease (5 mg/20 mL of extract) for 7 minutes at about 25° and centrifuged at 105,000×g for 1 hour. When there was a white film at the top of 105,000×g supernatant fluid, it was discarded and the remaining clear yellow supernatant fluids containing the cytochrome P-450 enzymes were used. In some cases (see, e.g., Example 30) instead of centrifuging at 105,000×g for 1 hr, the digested liquids were centrifuged at 50,000×g for 1 hour and the resulting supernatant fluids were used.

Total Protein Content Assay

The total protein content of the extracts was determined by the method of Lowry et al., J. Biol. Chem., 193:165–275, (1951).

Spectrophotometric Cytochrome P-450 Assay (CO-Difference Spectrophotometry)

Cytochrome P-450 was assayed by the method of Omura and Sato, J. Biol. Chem., 239:2370–2378, (1964), using a Perkin Elmer lambda 5 recording spectrophotometer. The extract (1 mL) was placed in both sample and reference cuvettes. The sample cuvette was reduced by the addition of a few crystals of sodium dithionite and the spectrum was recorded. Then the reference cuvette was reduced in the same fashion, and carbon monoxide was bubbled through the sample cuvette and the spectrum recorded. The O.D. at 448 nm was measured and the concentration of P-450 was calculated using a molar extinction coefficient of 91 $mM^{-1} \times cm^{-1}$ for the chromophore.

Quantitative Analysis of Genistein

These analyses were performed using a Du Pont 850 High Pressure Liquid Chromatograph (HPLC). Two solvent systems were used. Solvent A consisted of water and acetic acid in a ratio of 100:0.1 (v/v). Solvent B consisted of methanol and acetic acid in a ratio of 100:0.1 (v/v). A Du Pont C8 column was employed for the analyses and the injected samples were eluted with a mixture of 30% A and 70% B maintained isocratically at a flow rate of 1 mL×$min^{-1}$. The concentration of genistein in the samples was estimated using a calibration curve obtained from analysis of known quantities of genistein. Samples of cultures (2 ml) were mixed with ETOAC (1 mL), shaken vigorously and centrifuged. The organic layer (0.5 ml) was then dried under nitrogen, dissolved in 300 µL of MeOH, and analyzed by High Pressure Liquid Chromatography (HPLC). Using this system, genistein was eluted at 6.2 mL.

Analysis of Proteins by Gel Electrophoresis

Proteins in the 105,000×g supernatant fluids and desalted ammonium sulfate fractions thereof were analyzed by SDS-page electrophoresis (SDS=sodium dodecyl sulfate). For this purpose, 20 µL of sample containing approximately 5 mg per mL protein was added to 10 µL of SDS solubilizing buffer and heated at 95° for 3 minutes. SDS solubilizing buffer consists of 150 mM Na tricine (pH 7.8), obtained from Sigma Chemical Co., 150 mM dithiothreitol, 2.1% (w/v) glycerol 0.003% (w/v) bromphenol blue, and 6% lithium dodecyl sulfate. The entire 30 µL sample was then loaded onto a 15×32 cm 8% (or 10–17% gradient) polyacrylamide slab gel and electrophoresed overnight at 5–10 watts. After electrophoresis the gel was removed from the casting apparatus and the protein bands were stained with Coummassie blue.

Preparation of Phosphate Buffer Saline Solution (PBS w/Ca++ and Mg++)

The following ingredients were used to prepare the buffer: calcium chloride ($CaCl_2 2H_2O$; 0.7 mM); potassium chloride (KCl; 2.7 mM); potassium phospate monobasic ($KH_2PO_4$; 1.5 mM); magnesium chloride($MgCl_2$ $6H_2O$; 0.5 mM); sodium phosphate dibasic ($Na_2HPO_4$ $7H_2O$); 8.1 mM); and sodium chloride (NaCl;13.7 mM). The buffer was prepared by adding the following amounts of these ingredients, in the following order, to a suitable vessel containing 10 L of distilled, deionized water: $CaCl_2$ $2H_2O$—1.0 g; KCl—2.0 g; $KH_2PO_4$—2.0 g; NaCl—8.0 g; $MgCl_2$ $6H_2O$—1.0 g; and $Na_2HPO_4$ $7H_2O$—21.6 g. The mixture was stirred until all components were dissolved, and the solution then filter sterilized with a Millipore filter apparatus directly into 500 mL sterile screw-cap bottles. Next, 0.1 mL of the filtered solution was aseptically streaked on a complete base agar plate and the plate incubated for 24 hr at 37° to sterilize.

Preparation of Minimal Base Agar Plate

To prepare the minimal base agar plates, 60 g of Difco Bacto agar (granular), obtained from Difco Labs, Detroit, Mich. 48232, and 92.8 g of Davis Minimal Broth (dry form), obtained from Gibco Labs, Grand Island, N.Y. 14072, were suspended in 4000 mL of distilled, deionized water. The suspension was then stirred with a Teflon™ coated magnetic stirrer until the Minimal Broth was dissolved, and a sponge plug was placed in the top of flask and the flask covered with aluminum foil. The flask was then autoclaved for 20 minutes (15 psi, 121°). The flask was removed from the autoclave and, after 30 minutes, the contents stirred and dispensed onto a petri dish (25 mL per 100×15 mM petri plate (Falcon™ 1029) using Petrimat™ plate filling equipment. The filled petri plates were allowed to cool and stored at 4°.

Preparation of Complete Base Agar Plate

To prepare the complete base agar plates, 94.0 g of BBL Standard Methods agar (2.4%) (which contains, per liter, 5 g of pancreatic digest of casein, 2.5 g of yeast extract, 1 g of dextrose and 15 g of agar) was suspended in 4000 mL of distilled, deionized water. The suspension was stirred with a Teflon™ coated magnetic stirrer until the Standard Methods agar was dissolved, and a sponge plug was placed in the top of flask and the flask covered with aluminum foil. The flask was then autoclaved for 60 minutes (15 psi, 121°). The flask was removed from the autoclave and, after 30 minutes, the contents stirred and dispensed onto a petri dish (25 mL per 100×15 mM petri plate (Falcon™ 1029) using Petrimat™ plate filling equipment. The filled petri plates were incubated at 37° for 24 hr to check sterility and then stored at 4°.

Preparation of 0.5 mM L-Histidine/0.5 mM Biotin Solution

Approximately 450 mL of distilled, deionized water was added to a 500 mL volumetric flask containing 61.0 mg of D-biotin and 52.5 mg L-histidine, both obtained from Sigma Chemical Co., P.O. Box 14508, St. Louis, Mo. The flask was stirred until all components were dissolved and the flask brought to volume. The solution was then filter sterilized with a Nalgene 0.2 micron filter unit, produced by Nalgene Labware, Nalge Co., Rochester, N.Y. 14602. Next, 0.1 mL of the filtered solution was aseptically streaked on a complete base agar plate, the plates were incubated for 24 hr at 37° to check sterility, and 100 mL of the solution dispensed into each of five 100 mL bottles for storage at 4°.

Preparation of Top Agars

Standard top agar was prepared by first suspending 24.0 g of Difco Bacto agar and 24.0 g of sodium chloride (NaCl) in 4000 mL of distilled, deionized water. The solution was mixed and sterilized by autoclaving for 20 minutes at 121° (15 psi) and 75 mL dispensed into 100 mL capacity screw-cap bottles for storage at room temperature.

Procedure for Growing Cultures of *Salmonella* Strains

Suitable procedures for growing Salmonella cultures are well known in the art, and the particular procedure employed is not critical. The procedure employed in the Examples below is set forth in Maron et al., Mutation Research, 113:178–179 (1983).

EXAMPLES

Examples 1–10

Following the growth conditions described in the General Methods, organisms were transferred from sporulation agar stock slants or plates to 25 mL of Medium A and incubated with shaking at 2500 rpm at 28°–30° for three days—i.e., stage 1, Each strain was grown as a separate culture. Stage 2 cultures of each strain were prepared by inoculating 200 mL of medium A with 20 mL of stage 1 culture. Each stage 2 culture was incubated for 24 hours under the conditions used for stage 1 cultures. Each culture was processed separately and 105,000×g cell-extracts prepared separately using the Preparation of Cell Suspension and Cell Extracts procedures described in the General Methods. The yellow supernatant fluids were then assayed for cytochrome P-450 material using CO-Difference Spectrophotometry as discussed in the General Methods. The results are summarized below (Table 1).

TABLE 1

| Example | Medium | Organism | pmol P-450 per mg protein* |
|---|---|---|---|
| 1 | A | S. griseus, ATCC 13273 | 122.5 |
| 2 | A | S. griseus, ATCC 10137 | 28.2 |
| 3 | A | S. griseus, ATCC 13968 | 10.2 |
| 4 | A | S. griseus, ATCC 21897 | 2.3 |
| 5 | A | S. griseus, NRRL B-8090 | 53.6 |
| 6 | A | S. punipalus, NRRL 3529 | 6.2 |
| 7 | A | S. griseolus, ATCC 11796 | 5.3 |
| 8 | A | S. griseus, ATTC 23336 | <2.0 |
| 9 | A | S. griseus, NRRL 3242 | <2.0 |
| 10 | A | S. lincolnensis, ATCC 25466 | <2.0 |

*<2.0 means below measurable amounts

The above data illustrates the production of measurable amounts of cytochrome P-450 for a number of Streptomyces species and strains grown as described in medium A. The greatest amount of P-450 enzymes was produced by *S. griseus*, ATCC 13273. Although *S. griseus* ATTC 23336, *S. griseus*, NRRL 3242, and *S. lincolnensis*, ATCC 25466 failed to produce measurable amounts of P-450 enzymes in this experiment, it is believed that at higher inducer concentrations, measurable amounts would be present.

Examples 11–16

The procedures of Examples 1–10 were repeated except that the organisms were grown on Medium B (sporulation broth) and on medium C (nutrient broth). Only the three strains of Streptomyces producing the greatest amounts of cytochrome P-450 enzymes were used, namely, *S. griseus* ATCC 13273, ATCC 10137, and NRRL B-8090.

TABLE 2

| Example | Medium | Organism | pmol P-450 per mg protein* |
|---|---|---|---|
| 11 | B | S. griseus, ATCC 13273 | <2.0 |
| 12 | C | S. griseus, ATCC 13273 | <2.0 |
| 13 | B | S. griseus, ATCC 10137 | <2.0 |
| 14 | C | S. griseus, ATCC 10137 | <2.0 |
| 15 | B | S. griseus, NRRL B-8090 | <2.0 |
| 16 | C | S. griseus, NRRL B-8090 | <2.0 |

*<2.0 means below measurable amounts

As the data shows, the tested bacteria failed to produce measurable amounts of cytochrome P-450 enzymes on either media.

Examples 17–22

The procedures of Examples 1–10 were repeated except that cultures of *S. griseus*, ATCC 13273, were grown in the following media: Medium A having 5 g/L of soy oil substituted for the 5 g/L of soybean flour; Medium B with 5 g/L of soybean flour added; Medium B with 0.1 g/L of genistein added; Medium B with 0.1 g/L of coumestrol added; Medium B with 0.1 g/L of daidzein added; or Medium C with 5 g/L of soybean flour added. The amounts of cytochrome P-450 enzymes produced by each of comparable cultures is shown in Table 3. Soy oil, soybean flour, genistein, coumestrol and diadzein are all soybean derivatives. Soy oil, while containing many of the substituents of soybeans does not contain genistein.

TABLE 3

| Example | Medium | Substitution or Addition | pmol P-450 per mg protein* |
|---|---|---|---|
| 17 | A | with 5.0 g/L soy oil substituted for 5.0 g/L soybean flour | <2.0 |
| 18 | B | with 5.0 g/L soybean flour added | 28.0 |
| 19 | B | with 0.1 g/L genistein added | 124.8 |
| 20 | B | with 0.1 g/L coumestrol added | <2.0 |
| 21 | B | with 0.1 g/L daidzein added | <2.0 |

TABLE 3-continued

| Example | Medium | Substitution or Addition | pmol P-450 per mg protein* |
|---|---|---|---|
| 22 | C | with 5.0 g/L soybean flour added | 8.6 |

*<2.0 means below measurable amounts

Cytochrome P-450 enzymes were produced whenever soybean flour or genistein were present regardless of the media. Media without soybean flour or genistein but containing soy oil, coumestrol, or daidzein, all of which are soybean substituents, failed to induce cytochrome P-450 enzymes.

Examples 23-25

The procedures of Examples 1-10 were repeated except that cultures of S. griseus, ATCC 10137 were grown in the following media with the following added constituents: Medium B containing 5 g/L of soybean flour, or Medium B containing 0.1 g/L of genistein, or Medium C containing 5 g/L of soybean flour. The amounts of cytochrome P-450 enzymes produced by each culture are shown in Table 4.

TABLE 4

| Example | Medium | Addition | pmol P-450 per mg protein |
|---|---|---|---|
| 23 | B | soybean flour (5.0 g/L) | 6.1 |
| 24 | B | genistein (0.1 g/L) | 20.2 |
| 25 | C | soybean flour (5.0 g/L) | 4.9 |

Cytochrome P-450 enzymes were produced whenever soybean flour or genistein were present regardless of the medium.

Example 26

The procedures of Examples 1-10 were repeated except that a culture of S. griseus, NRRL B-8090 was grown in Medium B containing 0.1 g/L of genistein. The amount of cytochrome P-450 enzymes produced is shown in Table 5.

TABLE 5

| Example | Medium | Addition | pmol P-450 per mg protein |
|---|---|---|---|
| 26 | B | genistein (0.1 g/L) | 60.0 |

Significant cytochrome P-450 enzymes were produced.

From the data in Examples 1 through 26, it is clear that soybean flour and soybean flour substituents genistein and genistin can induce the production of cytochrome P-450 enzymes in bacteria from the genus Streptomyces.

Example 27

A three-day old stage 1 culture (200 mL) of S. griseus ATCC 13273 grown using the procedures in Examples 1-10 in Medium B was centrifuged and resuspended in 200 mL of fresh Medium B. The resulting suspension was added to a 1500 mL capacity fermenter vessel containing 1200 mL of the medium. Genistein (120 mg) was dissolved in about 3-4 mL of solvent consisting of dimethylformamide and methanol in a ratio of 3:2 (v/v), dimethylformamide:methanol, and the solution was added to the medium. Samples of 100-200 mL were removed periodically and their dry weight and cytochrome P-450 contents determined. The dry weight of each sample was measured by filtering 5 mL of the sample through a preweighed Nuclepore PC membrane (47 mm, 4 μm) filter and drying it overnight at 60°. The contents of cytochrome P-450 of each sample was determined essentially as in Examples 1-10. The results are shown in Table 6.

TABLE 6

| Time (h) | Dry wt. (mg/mL) | pmol P-450 per mg protein* |
|---|---|---|
| 0 | 0.326 | 3 |
| 7.5 | 0.314 | 12.5 |
| 23.5 | 0.408 | 30.3 |
| 48 | 1.54 | 56 |
| 72 | 1.18 | 19.3 |
| 96 | 1.3 | <2.0 |

*<2.0 means below measurable amounts

The results indicate that cytochrome P-450 is induced during the growth lag phase, reaches a maximum level between 48 and 72 hours, after which it diminishes and finally disappears at 96 hours. HPLC analysis of the supernatant fluids of batch cultures (shake flasks) containing genistein, conducted as described in the General Methods, Quantitative Analysis of Genistein section, indicate that during the induction and disappearance of cytochrome P-450, utilization of genistein does not occur.

Example 28

A stage 2 culture of S. griseus, ATCC 13273 grown for 24 hours in Medium A was harvested yielding 57.6 g wet weight of cells. An extract of these cells was obtained as described in Examples 1-10. After centrifugation at 105,000×g, a supernatant fluid of 102 mL was obtained. The supernatant fluid was fractionated by ammonium sulfate precipitation as follows. To obtain 35% of the saturation concentration of ammonium sulfate, 20.8 g of ammonium sulfate crystals were added to each 100 mL of the crude extract during a period of about 15 minutes with constant slow stirring. When the entire amount of salt was added, the stirring was continued for an additional 10 minutes to allow complete equilibration between dissolved and aggregated proteins. The cloudy liquid was centrifuged for 30 minutes at 18,000×g to separate the aggregated proteins. The pellet obtained in this fashion was labeled "0-35% pellet" and the supernatant fluid was labeled "0-35% supernatant". To each 100 mL of the "0-35% supernatant", 6.16 g of ammonium sulfate crystals were added, essentially as above, to obtain 45% of the saturation concentration. The cloudy solution was centrifuged, as above, to obtain the "35-45% pellet" and the "35-45% supernatant". A "45-55% pellet" and "45-55% supernatant" was obtained by adding, essentially as above, 6.38 g of ammonium sulfate crystals to each 100 mL of the "35-45% supernatant" followed by centrifugation, as above. The P-450 content of each of these fractions was determined as previously described in Examples 1-10. The total protein was determined in accordance with the General Methods, Total Protein Content Assay section. The pmol per mg protein was then calculated from the total protein and P-450 determinations. The results are summarized in Table 7.

TABLE 7

| Sample | Protein (mg/mL) | P-450 (pmol/mL) | pmol P-450 per mg protein |
|---|---|---|---|
| Crude | 12.5 | 749.4 | 59.9 |
| 0–35% supernatant | 7.4 | 560.0 | 75.6 |
| 0–35% pellet | 5.5 | 98.9 | 17.9 |
| 35–45% supernatant | 5.3 | 149.0 | 28.1 |
| 35–45% pellet | 38.4 | 5934.0 | 154.5 |
| 45–55% supernatant | 3.3 | 0.0 | 0.0 |
| 45–55% pellet | 45.4 | 1560.0 | 34.4 |

From the above data it is clear that the majority (almost 80%) of the cytochrome P-450 containing material is precipitated in the fraction resulting when the ammonium sulfate concentration was increased from 35% to 45% of the saturation level.

Example 29

Figure 1B:
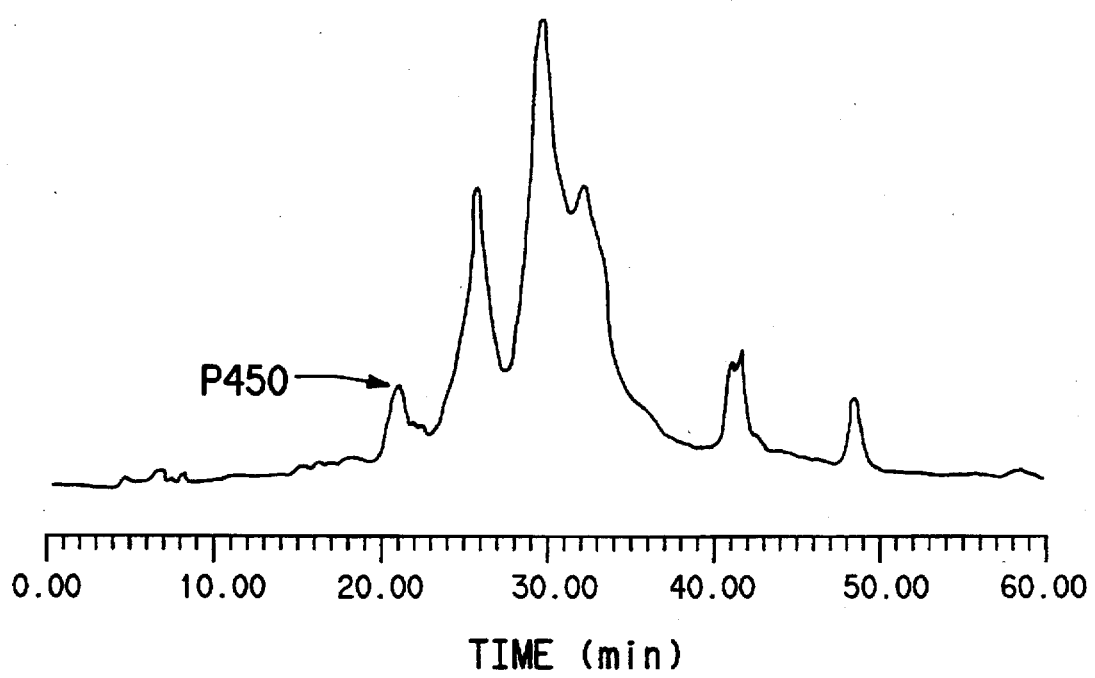

The 35–45% and 45–55% pellets of Example 28 were analyzed by Fast Protein Liquid Chromatography (FPLC) as follows. Sephadex G-25 (0.5 g/50 mL), obtained from Sigma Chemical Co., P.O. Box 14508, St. Louis, Mo. 63178, was stirred in DEP buffer. Some of the resulting gel was added to a 1.0 mL syringe containing a porous plug. The syringe was placed in a centrifuge tube and centrifuged in a bench-top centrifuge at 3000 rpm for 3 minutes. The addition of gel followed by centrifugation was repeated until the column was almost filled with the gel. The column was washed with 0.5 mL of buffer. A sample (150 µL) of the ammonium sulfate pellet dissolved in DEP buffer was added to the top of this column followed by centrifugation as before. The desalted protein extracts that accumulated in the centrifuge tube were then analyzed by FPLC using an LKB instrument connected to a Hewlett Packard (HP) diode array spectrophotometer, an HP 85 computer, and an HP plotter. Analyses were done using an LKB glaspac TSK DEAE-3SW (8×75 mm) anion exchange column. The solvent systems were as follows: Solvent A consisted of 20 mM tris acetate and 20% glycerol (pH 7.4); Solvent B consisted of solvent A with 0.8M sodium acetate added (pH 7.4). The gradient employed for the separation was 0–40 minutes; from 0–100% B. Fractions were eluted at a flow rate of 0.75 mL per minute and analyzed for cytochrome P-450 content as described above. The FPLC profiles at 420 nm can be seen in FIG. 1. Specifically, FIG. 1(A) shows the FPLC analysis of the 35–45% pellet fraction, and FIG. 1(B) shows the FPLC analysis of the 45–55% pellet fraction. The analyses indicate that in both ammonium sulfate fractions, the fractions eluting at 15 mL contained the cytochrome P-450 material.

Example 30

Oxidation of precocene II and 7-ethoxycoumarin with cell-free extracts

S. griseus, ATCC 13273 was grown in 200 mL of Medium A as described in Examples 1–10 except that at the beginning of stage 2,7-ethoxycoumarin (50 mg/200 mL) was added to one culture and precocene II (100 mg/ 200 mL) was added to another. Bacteria from these cultures were harvested after 24 hours of incubation in stage 2 and subjected to the French Pressure cell as described in Examples 1–10. The broken cells were centrifuged at 18,000×g for 10–15 minutes. The supernatant fluid of each was then centrifuged at 50,000×g for 1 hr. The resulting supernatant fluid constituted the test extract. Preparative scale incubations were performed using the test extract (1.5–20 mL), reduced nicotinamide adenins dinucleotide phosphate (NADPH) (77–101 mg) as cofactor and either precocene II (0.51 mg dissolved in 0.5 mL of an equal mixture of ethanol and water) or 7-ethoxycoumarin (0.66 mg was dissolved in 0.5 mL of an equal mixture of ethanol and water). The resulting mixtures were incubated on the shaker at 28° C. for 1.5 hours and then extracted with ½ volume of ethylacetate. The ethylacetate layer was dried under nitrogen and then taken up in a small volume of methanol for Thin Layer Chromatography (TLC) analysis. Products formed were isolated by preparative TLC using the solvent system of chloroform:methylene chloride:methanol:ethylacetate (10:10:1:1 v/v) for precocene metabolite, precocene-diol, and benzene:ethanol (45:5) for ethoxycoumarin metabolite, 7-hydroxycoumarin (umbelliferone). The bands corresponding to the precocene-diol and 7-hydroxycoumarin were then scraped off and the metabolites recovered from the silica gel by resuspending the scraped material in methanol and filtering the suspensions to remove the gel. The metabolites were recovered from the methanol by drying over anhydrous $MgSO_4$, under reduced pressure.

The metabolites obtained in this fashion were derivatized by the addition of a couple of drops of tetramethylsilane (TMS) and were then analyzed by Gas Chromatography/Mass Spectrometry (GC/MS). The TMS-derivatives of the metabolite isolated from the cell extract incubation with precocene II gave a molecular ion peak at m/e 398, a base peak at m/e 239 and another peak at m/e 73. The TMS-derivative of the isolated metabolite from incubation with 7-ethoxycoumarin gave a molecular ion peak at m/e 234, base peak at m/e 219, and major fragments at m/e 191, 163 and 73. These results are consistent with the GC/MS data for the TMS-derivatives of 7-hydroxycoumarin and trans-precocene-diol.

Example 31

In this example, a fluorometer was utilized to detect 7-ethoxycoumarin O-dealkylase activity. First, cells were grown on Medium A in the presence of ethoxy-coumarin and an extract was prepared as described in Example 30. Enzyme assays were performed by first adding test extract (1–2 mg of protein) to a 2 mL reaction mixture containing 0.05 mM ethoxycoumarin and DEP buffer, and then initiating the reaction by the addition of reduced nicotinamide adenine dinucleotide (NADH) (0.5 mM) as a cofactor. The formation of 7-hydroxycoumarin was determined by irradiating the cuvette at 365 mM and recording the increase in light emission at 450 nm using a fluorometer. Using this approach the specific activity for 7-hydroxycoumarin formation from 7-ethoxycoumarin was measured at about 0.2 $nmol \times min^{-1} \times mg^{-1}$ protein.

Examples 32–34

Cultures of S. griseus, ATCC 13273 were grown as described in Examples 1–10, except as follows. One culture was grown in Medium A, one culture in Medium B, and one culture in Medium B containing soybean flour at a concentration of 5 g/n. In addition, precocene II (100 mg/200 mL) was dissolved in 1 mL of methanol and added to the 24-hour stage 2 cultures. Samples (3 mL) were withdrawn after 48 hours. Each sample was extracted with ethylacetate (2 mL), thoroughly mixed, and centrifuged for 3 minute in a benchtop clinical centrifuge. The ethylacetate layer (1 mL) was withdrawn, dried under a stream of nitrogen and dissolved in 0.3 mL of methanol prior to HPLC analysis.

Quantitative analyses of precocene-diol formation were performed using a Du Pont 850 HPLC connected to a U. V. spectrophometer, a Waters WISP 710B automatic injector and a Perkin Elmer 56 recorder. The solvent systems used were: solvent A consisting of water and acetic acid in a ratio of 100 to 0.1, respectively; solvent B consisting of methanol and acetic acid in a ratio of 100 to 0.1, respectively. The gradient employed was 30–50% B for 6 minutes, 50–75% B for 2 min, 75–100% B for 5 minutes, isocratic at 100% B for 5 minute and then 100–30% B for 5 minutes. A calibration curve was prepared by injecting different volumes of a mixture of control 0.37 mg of cis- and 0.5 mg of trans-precocene- diol isomers. Samples were injected into a C8 column, eluted at a flow rate of 1 mL/minute and detected at 254 nm. Using this system, diols elute as a broad split peak at 16 mL while precocene elutes at 21 mL. The results are shown in Table 8.

TABLE 8

| formed (pmol/mg protein | Cytochrome P-450 formed (mg/mL at 48 h) | Precocene-diols Example Medium |
|---|---|---|
| 32 A | 122.5 | 1.27 |
| 33 B | <2.0 | 0.23 |
| 34 B + soybean flour | 28.0 | 0.87 |

HPLC analysis of the culture supernatants indicates the strong correlation between cytochrome P-450 concentrations and precocene-diol formation.

Example 35

Cultures of *S. griseus*, ATCC 13273, were grown on Medium A, on Medium B and on Medium B supplemented with genistein, and the 105,000×g supernatant fluid collected as described in Examples 1–10. A portion of the 105,000×g supernatant fluid from the culture grown on Medium A was then fractionated as described in Example 28. Analysis of the proteins present in the 105,000×g supernatant fluid from the cultures grown on unsupplemented and supplemented Medium B and the 35–45% and 45–55% ammonium sulfate pellet fractions from Medium A was accomplished using sodium dodecylsulfate polyacrylamide gel electrophoresis (SDS-page). For this purpose, 20 µL of each sample of the 105,000×g supernatant fluid, containing about 5 mg/mL of protein, was added to 10 µL of sodium dodecylsulfate solubilizing buffer and heated at 95° for 3 minutes. Each resulting 30 µL sample was then loaded onto a 15×32 cm gel containing 8% acrylamide and electrophoresed at pH 8.5, 0.1% sodium dodecyl sulfate, using a Protean slab cell (Bio-Rad) apparatus maintained at 5–10 W for 16.5 hours.

In addition, cultures of a mutant strain of *S. griseus* which lacks the ability to synthesize P-450 enzymes were grown on Medium A, and Medium B supplemented with genistein. The supernatant was collected and the proteins present in the 105,000×g supernatant fluid analyzed as described above.

Figure 2:
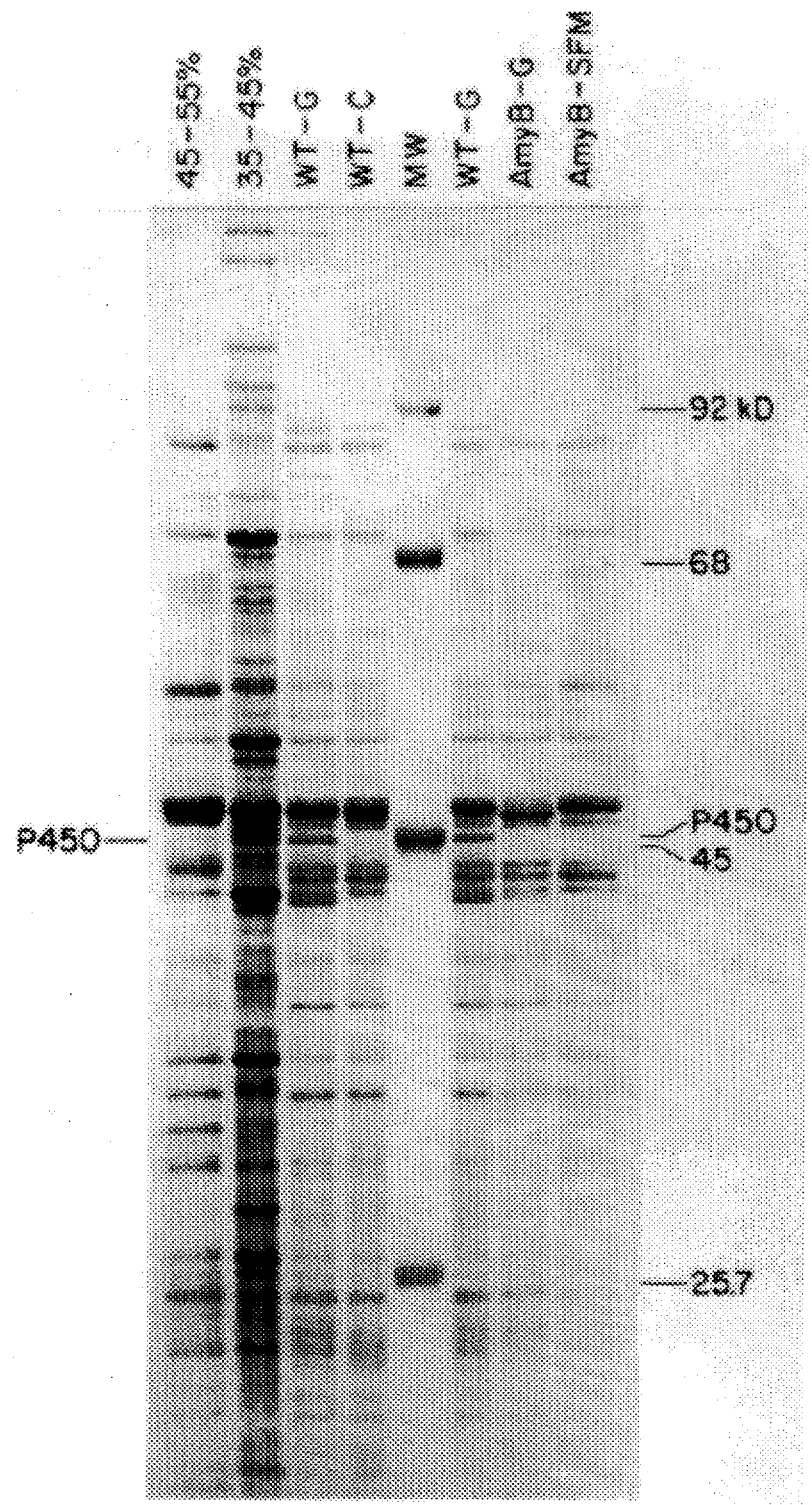
FIG. 2 shows the SDS-page gel electrophoresis of *S. griseus* extracts, as described in Example 32.

The results obtained after electrophoresis of proteins in the extracts described are shown in FIG. 2. In this figure, the lane designated MW represents the molecular weight standard. A polypeptide band with a molecular weight of 45,000 daltons was observed in extracts prepared from cells of *S. griseus*, ATCC 13273, grown on Medium B supplemented with genistein (lanes designated WT-B&G) but not in control cells grown on Medium B alone (lane designated WT-B). A band containing proteins of similar size was also detected in the 35–45% ammonium sulfate fractions of *S. griseus*, ATCC 13273, grown on Medium A (lane designated 35–45%), which, based on its relative stain intensity, appeared to have been enriched. This finding is consistent with the observation in Example 28 that P-450, as measured by CO-difference spectrophotometry, was contained primarily in the 35–45% ammonium sulfate fraction. Finally, little or none of a 45,000 molecular weight protein could be detected in the mutant strain grown on Medium A (lane designated M-A) and Medium B with genistein (lane designated M-B&G). These results lead one to conclude that a 45,000 dalton peptide represents the major cytochrome P-450 protein induced by either genistein or soybean.

Example 36

Three cultures of *S. griseus*, ATCC 13273 were grown on Medium B as described in Examples 1–10, except that at the beginning of stage 2 growth, one of three classical mammalian P-450 inducers—see, e.g., Bresnick et al., Pharmacological Reviews, 36:43S, (1984) (3-methylcholanthrene); Richardson et al., Cancer Res., 11:274, (1951) (3-methylcholanthrene); Conney, A. H., Pharmacol. Rev., 19:317 (1966) (phenobarbital) and Ames et al., Mutation Res., 31:347, (1975) (3-methyl-cholanthrene, phenobarbital and aroclor)—were added to each of the cultures. Specifically, the inducers employed were: (1) phenobarbital added to a concentration of 0.25 mg/mL of culture; (2) 3-methyl-cholanthrene added to a concentration of 0.25 mg/mL of culture; and (3) aroclor added to a concentration of 1 mL/200 mL of culture. The bacteria were harvested after 24 hours of incubation and the amount of cytochrome P-450 in each sample determined as described in Examples 1–10.

The culture containing phenobarbital produced 5.21 pmol/mg protein of cytochrome P-450 material. The culture containing 3-methylcholanthrene produced 2.72 pmol/mg protein of cytochrome P-450 material.

Example 37

Three cultures of *S. griseus*, ATCC 13273 were grown on Medium B as described in Examples 1–10, except that at the beginning of stage 2 growth, all three cultures received soybean flour to a concentration of 5 g/L. One culture received no further additions, one culture received metyrapone, a classic mammalian P-450 inhibitor of cytochrome P-450 induction in mammalian systems, see, e.g., Ryan et al., Methods in Enzymology, L11:117–132 (1978), to a concentration of 0.1 mg/mL, and the remaining culture received metyrapone to a concentration of 0.25 mg/mL. The cultures were incubated an additional 24 hr before the amount of cytochrome P-450 produced by each was determined, as described in Examples 1–10. The culture with soybean flour produced 15.71 pmol of cytochrome P-450 material per mg or total protein. The cultures with metyrapone at 0.1 mg/mL and 0.25 mg/mL produced 25.1 and 38.7 pmol of cytochrome P-450 material, respectively. Clearly metyrapone did not inhibit, but rather stimulated, the production of cytochrome P-450 material, illustrating the difference between the production of mammalian and *S. griseus*, P-450.

Example 38

Two cultures of *S. griseus*, ATCC 13273 were grown in Medium A essentially as described in Examples 1–10. A 200 mL stage 2 culture of each was prepared. At this time, 20 mg of Benzo[a]pyrene (BZP) which had been dissolved in 1 mL of dimethylsulfoxide was added to one of the cultures. The other culture served as a control. Both cultures were incubated, with shaking, for 24 hours. The bacteria were then collected by centrifuging them at 9,000×g for 20 minutes. The supernatant fluids (200 mL from each) were then extracted with ½ volume of ethylacetate and the resulting solutions dried under nitrogen. The dried residue from each were resuspended in 0.8 mL of dimethylsulfoxide, and 0.1 mL of the control supernatant fluids (control extract) and 0.1 mL of the BZP-treated supernatant fluids (BZP extract) was added to each of two agar plates along with the histidine requiring mutant strain of *Salmonella typhimurium*, strain TA 98, used in the Ames assay to detect mutagenic chemicals. In addition, 0.1 mL of the BZP-treated supernatant fluids was added to *Salmonella typhimurium*, strain TA 98, together with an Ames test rat microsomal S9 preparation (BZP extract+rat microsomes S9). Samples are considered to contain potential mutagenic compounds if the number of colonies—arising from a revertant mutation—on the plates containing the material being tested is two-fold or greater than the number of colonies on the plates seeded with bacteria which have not seen any additional chemicals. The latter constitute the controls and colonies arising in cultures of them represent spontaneous mutations. The results of this experiment are shown in Table 9.

TABLE 9

| Extract | Revertants/plate (2 plates shown) |
|---|---|
| control extract | 166,179 |
| BZP extract | 458,425 |
| BZP extract + rat microsomes S9 | 832,755 |

These results show that *S. griseus*, can metabolize BZP to its mutagenic forms and serve as a potential replacement for rat microsomal S9 preparations. Use of *S. griseus*, for this test eliminates the requirements for rat microsomes with the required cofactor which are two major expenses of the Ames test as now routinely performed.

Examples 39–46

*S. griseus*, (ATCC 13273) was grown on a soybean/glycerol medium according to the two-stage fermentation protocol. Procarcinogen substrates (20 mg/200 mL culture) were added to the 24 hr old second stage cultures and incubated at 28° for 24 hr. Incubations were then harvested by centrifuging (30 minutes, 10,000×g, 4°) and both supernatants (Spt) and the pellets (P) were used for the Salmonella assay. *Salmonella typhimurium* strains used in these tests were TA 98 and TA 1538. The procarcinogens employed were: 2-aminoanthracene, 3,3- dimethylbenzidine, 3,3'-dimethyloxybenzidine, Benzo(a)pyrene, chloropicrin, benzidine, 2-aminoacetylfluorene and 7,12-dimethylbenzanthracene. Controls in these experiments consisted of: (1) samples of cell-free supernatant fluid (Spt) and pellets (P) of *S. griseus*, 24 hr old second stage cultures incubated without any procarcinogens (*S. griseus*, control); (2) samples of procarcinogens in soybean/glycerol medium without *S. griseus*, incubated for 24 hr at 28° (procarcinogen control); and/or (3) samples of procarcinogens directly applied to the Salmonella strains (Direct Application).

Assay procedure:

The procedures for preparation of the histidine/biotin solution and top agar used, and the growth conditions employed for the Salmonella strains are discussed in the General Methods. For the assay, 500 µL of the samples to be tested (in the indicated dilutions) and 100 µL of the TA strains were mixed in tubes by vigorous shaking and incubated with shaking at 37° for 1 hr. Separately, to 75 mL of top agar was added 10 mL of histidine/biotin solution. The volume was brought up to 100 mL with sterile distilled, deionized water, and 100 µL of a 50 mg/mL solution of thiostrepton dissolved in dimethylsulfoxide (DMSO) was added. Two mL of the top agar containing the above additions was then added to the incubated tubes and the mixture poured on an agar plate. The plates were incubated at 37° for 48 hr and the number of Salmonella colonies counted.

Results of the experiments are presented in the following tables. High numbers of Salmonella revertants were observed for the procarcinogens incubated with *S. griseus*, indicating that *S. griseus*, can metabolize these chemicals to mutagenic metabolites. The following abbreviations found in the Tables are defined as follows: und=undiluted; 1:2= diluted twice; 1:10=diluted ten times; 1:100=diluted a hundred times; and NT=not tested.

Example 39

2-Aminoanthracene (Procarcinogen)

| | | # of Salmonella revertants | |
|---|---|---|---|
| | dilutions | TA 98 | TA 1538 |
| *S. griseus* control (Spt) | und | 5.5 | 2 |
| | 1:2 | 8 | 3.5 |
| | 1:10 | 8 | 2 |
| | 1:100 | 7.5 | 1 |
| *S. griseus* control (P) | und | 7.5 | 5 |
| | 1:2 | 14.5 | 8 |
| | 1:10 | 12 | 11.5 |
| | 1:100 | 6.5 | 6 |
| *S. griseus* test (Spt) | und | 351 | 132 |
| | 1:2 | 195.5 | 130 |
| | 1:10 | 49.5 | 33.5 |
| | 1:100 | 16 | 9.5 |
| *S. griseus* test (P) | und | 758 | 602 |
| | 1:2 | 1295 | 1122 |
| | 1:10 | 582 | 555 |
| | 1:100 | 52.5 | 66 |
| 2-aminoanthracene control (Spt) | und | 26 | 730 |
| | 1:2 | 22.5 | 312.5 |
| | 1:10 | 12.5 | 57.5 |
| | 1:100 | 4.5 | 7.5 |
| 2-aminoanthracene control (P) | und | 37 | 28 |
| | 1:2 | 61 | 21 |
| | 1:10 | NT | 46.5 |
| | 1:100 | NT | 54 |

Example 40

3,3'-dimethylbenzidine (Procarcinogen)

| | | # of Salmonella revertants | |
|---|---|---|---|
| | dilutions | TA 98 | TA 1538 |
| *S. griseus* control (Spt) | und | 22 | 3 |
| | 1:2 | 12 | 6 |
| | 1:10 | 11 | 4 |
| | 1:100 | 8 | 2 |
| *S. griseus* control (P) | und | 12 | 12 |
| | 1:2 | 45 | 18 |
| | 1:10 | 18 | 12 |
| | 1:100 | 13 | 6 |
| *S. griseus* test (Spt) | und | 1862 | 2048 |
| | 1:2 | 44 | 38 |
| | 1:10 | 17 | 10 |
| | 1:100 | 16 | 6 |

3,3'-dimethylbenzidine (Procarcinogen)

| | | # of Salmonella revertants | |
|---|---|---|---|
| | dilutions | TA 98 | TA 1538 |
| S. griseus test | und | 593 | 478 |
| (P) | 1:2 | 216 | 331 |
| | 1:10 | 134 | 188 |
| | 1:100 | 24 | 25 |
| 3,3'-dimethylbenz- | und | 28 | 30 |
| idine control (Spt) | 1:2 | 18 | 22 |
| | 1:10 | 22 | 11 |
| | 1:100 | 19 | 8 |
| 3,3'-dimethylbenz- | und | 20 | 15 |
| idine control (P) | 1:2 | 22 | 13 |
| | 1:10 | 17 | 9 |
| | 1:100 | 13 | 8 |
| Direct Application | und | 9 | 16 |
| | 1:2 | 10 | 11 |
| | 1:10 | 16 | 8 |

Example 41

3,3'-dimethoxybenzidine (Procarcinogen)

| | | # of Salmonella revertants | |
|---|---|---|---|
| | dilutions | TA 98 | TA 1538 |
| S. griseus control | und | 15 | 16 |
| (Spt) | 1:2 | 17 | 9 |
| | 1:10 | 17 | 2 |
| | 1:100 | 24 | 1 |
| S. griseus control | und | 19 | 7 |
| (P) | 1:2 | 26 | 15 |
| | 1:10 | 22 | 9 |
| | 1:100 | 15 | 4 |
| S. griseus test | und | 76 | 55 |
| (Spt) | 1:2 | 42 | 43 |
| | 1:10 | 32 | 14 |
| | 1:100 | 21 | 10 |
| S. griseus test | und | 930 | 799 |
| (P) | 1:2 | 259 | 300 |
| | 1:10 | 314 | 500 |
| | 1:100 | 26 | 16 |
| 3,3'-dimethoxybenz- | und | 63 | 35 |
| idine control (spt) | 1:2 | 31 | 12 |
| | 1:10 | 25 | 6 |
| | 1:100 | 19 | 5 |
| 3,3'-dimethoxybenz- | und | 11 | 22 |
| idine control (P) | 1:2 | 12 | 14 |
| | 1:10 | 6 | 11 |
| | 1:100 | 11 | 9 |
| Direct Application | und | 12 | 15 |
| | 1:2 | 9 | 7 |
| | 1:10 | 8 | 5 |
| | 1:100 | 6 | 5 |

Example 42

Benzo(a)pyrene (Procarcinogen)

| | | # of Salmonella revertants | |
|---|---|---|---|
| | dilutions | TA 98 | TA 1538 |
| S. griseus control | und | 22 | 3 |
| (Spt) | 1:2 | 12 | 6 |
| | 1:10 | 11 | 4 |
| | 1:100 | 8 | 2 |
| S. griseus control | und | 12 | 12 |
| (P) | 1:2 | 45 | 18 |

Benzo(a)pyrene (Procarcinogen)

| | | # of Salmonella revertants | |
|---|---|---|---|
| | dilutions | TA 98 | TA 1538 |
| | 1:10 | 18 | 12 |
| | 1:100 | 13 | 6 |
| S. griseus test | und | 100 | 23 |
| (Spt) | 1:2 | 110 | 31 |
| | 1:10 | 43 | 15 |
| | 1:100 | 9 | 10 |
| S. griseus test | und | 414 | 338 |
| (P) | 1:2 | 311 | 258 |
| | 1:10 | 233 | 206 |
| | 1:100 | 82 | 72 |
| Benzo(a)pyrene | und | 27 | 10 |
| control (Spt) | 1:2 | 29 | 8 |
| | 1:10 | 18 | 8 |
| | 1:100 | 17 | 2 |
| Benzo(a)pyrene | und | 18 | 11 |
| control (P) | 1:2 | 17 | 15 |
| | 1:10 | 12 | 8 |
| | 1:100 | 14 | 10 |

Experiment 43

Chloropicrin, 100 µl (Procarcinogen)

| | | # of Salmonella revertants | |
|---|---|---|---|
| | dilutions | TA 98 | TA 1538 |
| S. griseus control | und | 8 | 9 |
| (Spt) | 1:2 | 8 | 5 |
| | 1:10 | 6 | 5 |
| | 1:100 | 5 | 4 |
| S. griseus control | und | 14 | 22 |
| (P) | 1:2 | 26 | 19 |
| | 1:10 | 17 | 14 |
| | 1:100 | 17 | 6 |
| S. griseus test | und | 115 | 33 |
| (Spt) | 1:2 | 50 | 21 |
| | 1:10 | 13 | 10 |
| | 1:100 | 10 | 4 |
| S. griseus test | und | 72 | 29 |
| (P) | 1:2 | 17 | 12 |
| | 1:10 | 10 | 7 |
| | 1:100 | 11 | 3 |
| Chloropicrin | und | 19 | 14 |
| control (Spt) | 1:2 | 22 | 8 |
| | 1:10 | 9 | 3 |
| | 1:100 | 5 | 0 |
| Chloropicrin | und | 15 | 24 |
| control (P) | 1:2 | 10 | 5 |
| | 1:10 | 5 | 3 |
| | 1:100 | 12 | 4 |
| Direct Application | und | 13 | 6 |
| | 1:2 | 11 | 4 |
| | 1:10 | 10 | 6 |
| | 1:100 | 11 | 6 |

Example 44

Benzidine (Procarcinogen)

| | | # of Salmonella revertants | |
|---|---|---|---|
| | dilutions | TA 98 | TA 1538 |
| S. griseus control | und | 22 | 13 |
| (Spt) | 1:2 | 18 | 8.5 |
| | 1:10 | 21 | 6 |

-continued

| Benzidine (Procarcinogen) | | | |
|---|---|---|---|
| | | # of Salmonella revertants | |
| | dilutions | TA 98 | TA 1538 |
| | 1:100 | 10 | 9.5 |
| S. griseus control | und | 12 | 16.5 |
| (P) | 1:2 | 25 | 11.5 |
| | 1:10 | 20 | 9 |
| | 1:100 | 23 | 5.5 |
| S. griseus test | und | 246 | 315 |
| (Spt) | 1:2 | 38 | 32 |
| | 1:10 | 23 | 12.5 |
| | 1:100 | 12 | 4.5 |
| S. griseus test | und | 478 | 764 |
| (P) | 1:2 | 169 | 99.5 |
| | 1:10 | 133 | 88 |
| | 1:100 | 18 | 12.5 |
| Benzidine | und | 53 | 17.5 |
| control (Spt) | 1:2 | 33 | 8 |
| | 1:10 | 18 | 7 |
| | 1:100 | 13 | 6.5 |
| Benzidine | und | 16 | 6.5 |
| control (P) | 1:2 | 13 | 4 |
| | 1:10 | 15 | 3 |
| | 1:100 | 13 | 10.5 |

Example 45

| 7,12-dimethylbenzanthracene (Procarcinogen) | | | |
|---|---|---|---|
| | | # of Salmonella revertants | |
| | dilutions | TA 98 | TA 1538 |
| S. griseus control | und | 14 | 9.5 |
| (Spt) | 1:2 | 10.5 | 7.5 |
| | 1:10 | 6.5 | 4.5 |
| | 1:100 | 16 | 4.5 |
| S. griseus control | und | 8.5 | 0.5 |
| (P) | 1:2 | 26.5 | 7 |
| | 1:100 | 48.5 | 5.5 |
| S. griseus test | und | 42.5 | 20.5 |
| (Spt) | 1:2 | 41 | 13.5 |
| | 1:10 | 31 | 8 |
| | 1:100 | 34 | 8.5 |
| S. griseus test | und | 39 | 15.5 |
| (P) | 1:2 | 86.5 | 54.5 |
| | 1:10 | 103 | 108 |
| | 1:100 | 4.25 | 37 |
| 7,12-dimethylbenz- | und | | |
| anthracene | | | |
| control (Spt) | | | |

Example 46

| 2-Aminoacetylfluorene (Procarcinogen) | | | |
|---|---|---|---|
| | | # of Salmonella revertants | |
| | dilutions | TA 98 | TA 1538 |
| S. griseus control | und | 5.5 | 2 |
| (Spt) | 1:2 | 13 | 3.5 |
| | 1:10 | 11 | 2 |
| | 1:1002 | 17 | 1 |
| S. griseus control | und | 11.5 | 5 |
| (P) | 1:2 | 17.5 | 8 |
| | 1:10 | 20.5 | 11.8 |
| | 1:100 | 20.5 | 6 |
| S. griseus test | und | 93.5 | 2 |
| (Spt) | 1:2 | 56 | 4 |

-continued

| 2-Aminoacetylfluorene (Procarcinogen) | | | |
|---|---|---|---|
| | | # of Salmonella revertants | |
| | dilutions | TA 98 | TA 1538 |
| | 1:10 | 30 | 7 |
| | 1:100 | 17.5 | 7 |
| S. griseus test | und | 5000 | 299 |
| (P) | 1:2 | 1175 | 262.5 |
| | 1:10 | 467.5 | 67.5 |
| | 1:100 | 322.5 | 11 |
| 2-aminoacetyl- | und | NT | 4 |
| fluorene control | 1:2 | NT | 8.5 |
| (Spt) | 1:10 | NT | 4 |
| | 1:100 | NT | 0.5 |
| 2-aminoacetyl- | und | NT | 26 |
| fluorene | 1:2 | NT | 21 |
| control (P) | 1:10 | NT | 12 |
| | 1:100 | NT | 6 |

Example 47

Shake flasks containing 25 mL of soybean-glycerol medium were inoculated, respectively, with approximately $10^4$ to $10^5$ spores/flask of S. griseus ATCC 13273, S. griseus (pH63) and S. griseus (pFS). The medium in the flasks receiving S. griseus (pH63) and S. griseus (pFS) also contained thiostrepton (Ts) at a concentration of 20 µg/mL. The flasks were incubated for 72 hours at 27° to 28° C., and constantly shaken at 150 to 200 RPM. (Stage 1 cultures)

From each of the resulting cultures, 2 mL were removed and added to two new flasks with 25 mL of soybean-glycerol medium and appropriately supplemented with Ts for those receiving S. griseus (pH63) and S. griseus (pFS). These six secondary cultures were incubated for 24 hours at 27° to 28° C. (Stage two cultures)

Benzo(a)pyrene (BZP), (5 mg) in 200 µl of solvent (50% DMSO, 50% Acetone, v/v) was added to one flask of each culture. The other flask of each culture received only solvent (100 µl). All the cultures were incubated for 24 hours at 27° to 28° C.

The bacterial cells from each culture were collected and washed three times with sterile 50 mM sodium phosphate buffer, pH 7.0 and resuspended in 0.3 mL of buffer. From each culture, 50 µL were plated onto each of 5 plates of M7 agar. The M7 agar onto which the cultures containing S. griseus (pH63) and S. griseus (pFS) were plated also contained 10 µg/mL of Ts. Spores were harvested and titered on M7Ts and M7Km and the ratio of revertants to kanamycin resistance between those cultured in the presence and absence of benzo(a)pyrene determined.

Results:

| | Frequence of Reverants | | |
|---|---|---|---|
| Strains | No BZP | BZP | Mutagenic Ratio |
| 13273 (Ts) | none | none | NA |
| 13273 (Km) | none | none | NA |
| H63 | $2.8 \times 10^{-5}$ | $3.7 \times 10^{-5}$ | 1.32 |
| FS | $4.1 \times 10^{-8}$* | $3.4 \times 10^{-8}$* | 0.83* |

*There were so few reverants of S. griseus (pFS) spores that these numbers may be inaccurate.

Example 48

S. griseus (pH69) and S. griseus (pFS) were grown through stage 1 and stage 2 cultures as in Example 47. After the 24 hours of growth in stage 2, 5 mg per flask of each of the following mutagens dissolved in 750 µl DMSO were added to one culture each of S. griseus (pH69) and S. griseus (pFS) (one culture each of S. griseus (pH69) and S. griseus (pFS) received only DMSO and served as the controls): benzo(a)pyrene (BZP), 2-aminoanthracene (2AA), Ethidium bromide (EtBr), Mutagen ICR-191 (ICR191). The flasks were incubated for three hours (shaking) with mutagens, then 1 mL of each culture was harvested from each of the shake flasks, and the bacteria recovered from each of the samples were washed three times with phosphate buffer and resuspended in a small amount of buffet (100 µL for each aliquot to be plated). Aliquots of these suspensions (100 µl) were spread on each of 5 M7Ts plates and incubated for spore formation. After 72 more hours, the spores were harvested and titered on M7Ts and M7Km plates.

Results:

| Strain | Mutagen | Km titer | Ts titer | Rev. Freq. | Mut. Ratio |
|---|---|---|---|---|---|
| pH69 | Control | $1.15 \times 10^1$ | $2.65 \times 10^8$ | $4.3 \times 10^{-8}$ | 1.0 |
|  | EtBr | none | none | none | NA |
|  | BZP | $6.5 \times 10^1$ | $1.3 \times 10^8$ | $5.0 \times 10^{-7}$ | 11.6 |
|  | ICR191 | $2.5 \times 10^1$ | $2.65 \times 10^8$ | $9.4 \times 10^{-8}$ | 2.2 |
|  | 2AA | $2.0 \times 10^1$ | $2.25 \times 10^8$ | $8.8 \times 10^{-8}$ | 2.0 |
| pFS | Control | $8.7 \times 10^3$ | $5.7 \times 10^7$ | $1.5 \times 10^{-4}$ | 1.0 |
|  | EtBr | — | — | — | NA |
|  | BZP | $4.3 \times 10^3$ | $1.7 \times 10^7$ | $2.5 \times 10^{-4}$ | 1.7 |
|  | ICR191 | $8.0 \times 10^3$ | $1.9 \times 10^7$ | $4.2 \times 10^{-4}$ | 2.8 |
|  | 2AA | $1.33 \times 10^4$ | $1.2 \times 10^7$ | $1.1 \times 10^{-3}$ | 7.3 |

1) The concentration of ethidium bromide used was lethal to the cells.
2) The stock vials of this batch of FS were discarded after this experiment due to the abnormally high revertant frequency of the control cultures.

Example 49

S. griseus (pH69) and S. griseus (pFS) were grown through stage 1 and stage 2 cultures as in Example 47. After the 24 hours of growth in stage 2, 1 mg per flask of each of the following mutagens was added to one culture each of S. griseus (pH69) and S. griseus (pFS) (one culture each of S. griseus (pH69) and S. griseus (pFS) received only DMSO and served as the controls): N-methyl-N'-nitro-N-nitrosoguanidine (NTG), benzo(a)pyrene (BZP), 2-aminoanthracene (2AA), Mutagen ICR-191 (ICR191). Note: In order to reduce the chances of toxicity, the mutagens were added at a concentration of 1 mg/25 mL culture volume in 200 µl DMSO. These cultures were incubated for 6 hours (instead of 3h as in Example 48), with shaking, to compensate for the reduced concentration of mutagens. An aliquot of 1 mL of each culture was harvested from each of the shake flasks, and the bacteria recovered from each of the samples were washed three times with phosphate buffer and resuspended in a small amount of buffer. An aliquot (100 µL) of each of these suspensions was spread on each of 5 Yeast extract-glycerol plates contining Ts at a concentration of 10 µg/mL and incubated for spore formation. After 72 more hours, the spores were harvested and titered on M7Ts and M7Km plates.

Note:

Yeast extract-glycerol medium is the same as soybean-glycerol medium without soybean. These plates gave poor spore formation, and, as such, the spore preparations may have contained multicellular mycelial fragments which may have lead to an altered revertant frequency.

Results:
Titers indicate the average number of colony

| Strain | Chemical | Ts Titer | Km Titer | Rev. Freq. | Mut. Ratio |
|---|---|---|---|---|---|
| pH69 | DMSO | $1.20 \times 10^8$ | $5.50 \times 10^2$ | $4.6 \times 10^{-6}$ | 1.0 |
|  | NTG | $3.70 \times 10^8$ | $1.25 \times 10^4$ | $3.4 \times 10^{-5}$ | 7.4 |
|  | BZP | $2.20 \times 10^8$ | $2.35 \times 10^3$ | $1.1 \times 10^{-5}$ | 2.4 |
|  | 2AA | $2.55 \times 10^8$ | $1.75 \times 10^3$ | $6.9 \times 10^{-6}$ | 1.5 |
|  | ICR191 | $2.25 \times 10^8$ | $1.75 \times 10^2$ | $7.8 \times 10^{-7}$ | 0.2 |
| pFS | DMSO | $2.90 \times 10^8$ | $2.85 \times 10^3$ | $9.8 \times 10^{-7}$ | 1.0 |
|  | NTG | $3.05 \times 10^7$ | $8.00 \times 10^1$ | $2.6 \times 10^{-6}$ | 2.7 |
|  | BZP | $3.15 \times 10^7$ | $2.00 \times 10^1$ | $6.3 \times 10^{-7}$ | 0.6 |
|  | 2AA | $5.50 \times 10^7$ | $7.50 \times 10^1$ | $1.4 \times 10^{-6}$ | 1.4 |
|  | ICR191 | $3.45 \times 10^7$ | $1.50 \times 10^1$ | $4.3 \times 10^{-7}$ | 0.4 | forming units per milliliter of spore preparation.

Example 50

S. griseus (pH69) and S. griseus (pFS) were grown through stage 1 and stage 2 cultures as in Example 47. After the 24 hours of growth in stage 2, 5 mg per flask of each of the following mutagens were added to one culture each of S. griseus (pH69) and S. griseus (pFS) (one culture each of S. griseus (pH69) and S. griseus (pFS) received only DMSO and served as the controls): N-methyl-N'-nitro-N-nitrosoguanidine (NTG), benzo(a)pyrene (BZP), 2-aminoanthracene (2AA), Mutagen ICR-191 (ICR191). The resulting cultures were incubated for 24 hours, with shaking. Cells (1 mL) from each culture were harvested, and the bacteria recovered from each were washed three times with phosphate buffer and resuspended in a small amount of buffer. An aliquot (100 µL) of each of these suspensions was spread on Yeast extract-glycerol plates containing Ts at a concentration of 10 µg/mL and incubated for spore formation. After 72 more hours, the spores were harvested and titered on M7Ts and M7Km plates.

The cells treated with NTG gave very sparse growth for spore formation. It is assumed this was due to the toxicity of the compound.

Also, the fact that cells grown on Yeast extract-glycerol Ts medium do not yield as many spores as when they are grown on other media such as M7Ts agar was noted in Example 49.

Results:

| Strain | Mutagen | Km Titer | Ts Titer | Rev. Freq. | Mut. Ratio |
|---|---|---|---|---|---|
| pH69 | solvent | $6.33/10^2$ | $3.90/10^7$ | $1.62/10^{-5}$ | 1.0 |
|  | BZP | $6.33/10^2$ | $3.23/10^7$ | $1.96/10^{-5}$ | 1.2 |
|  | NTG | $5.03/10^2$ | $4.27/10^6$ | $1.18/10^{-4}$ | 7.3 |
|  | 2AA | $1.27/10^3$ | $4.73/10^7$ | $2.68/10^{-5}$ | 1.65 |
|  | ICR191 | $3.13/10^2$ | $1.77/10^7$ | $1.76/10^{-5}$ | 1.1 |
| pFS | solvent | $3.67/10^1$ | $8.67/10^7$ | $4.23/10^{-7}$ | 1.0 |
|  | BZP | $9.67/10^1$ | $1.50/10^8$ | $6.44/10^{-7}$ | 1.5 |
|  | NTG | $6.67/10^0$ | $1.40/10^7$ | $4.76/10^{-7}$ | 1.13 |
|  | 2AA | $3.03/10^2$ | $1.87/10^8$ | $1.62/10^{-6}$ | 3.8 |
|  | ICR191 | $1.50/10^1$ | $5.97/10^7$ | $2.51/10^{-7}$ | 0.6 |

Example 51

S. griseus pH69) was grown through stage 1 and stage 2 cultures as in Example 47. After the 24 hours of growth in stage 2, 5 mg per flask of benzo(a)pyrene were dissolved in different sovents or at different concentrations aria added to one culture of S. griseus (pH69) (a culture of S. griseus (pH69) received only solvent and served as the controls). The resulting cultures were incubated for 24 hours, with shaking. Cells (1 mL) from each culture were harvested, and the bacteria recovered from each were washed three times with phosphate buffer and resuspended in a small amount of buffer. An aliquot (1.0 mL) of each of these suspensions was spread on M7Ts agar plates containing Ts at a concentration of 10 μg/mL and incubated for spore formation. After 72 more hours, the spores were harvested and titered on M7Ts and M7Km plates.

Results:

| Solvent | Mutagen | Km Titer | Ts Titer | Rev. Freq. | Mut. Ratio |
|---|---|---|---|---|---|
| *DMSO + Acetone | none | $7.33 \times 10^1$ | $4.20 \times 10^8$ | $1.75 \times 10^{-7}$ | — |
| *DMSO + Acetone | BZP | $1.30 \times 10^2$ | $6.90 \times 10^8$ | $1.88 \times 10^{-7}$ | 1.07 |
| Acetone (300 μL) | none | $1.40 \times 10^2$ | $7.23 \times 10^8$ | $1.94 \times 10^{-7}$ | — |
| Acetone (300 μL) | BZP | $1.63 \times 10^2$ | $4.40 \times 10^8$ | $3.70 \times 10^{-7}$ | 1.91 |
| DMSO (750 μL) | none | $1.40 \times 10^2$ | $6.43 \times 10^8$ | $2.17 \times 10^{-7}$ | — |
| DMSO (750 μL) | BZP | $5.47 \times 10^2$ | $5.53 \times 10^8$ | $9.88 \times 10^7$ | 4.55 |
| DMSO (1500 μL) | none | $1.57 \times 10^2$ | $4.97 \times 10^8$ | $3.50 \times 10^{-7}$ | — |
| DMSO (1500 μL) | BZP | $1.51 \times 10^3$ | $4.27 \times 10^8$ | $3.55 \times 10^{-6}$ | 11.27 |

*Mixture contained 200 μL of DMSO and 100 μL of Acetone
Note: Many of the Km$^r$ colonies of the cells incubated with BZP in 750 μL and 1500 μL of DMSO were very small.

Example 52

*S. griseus* (pH69) and *S. griseus* (pFS) were grown through stage 1 and stage 2 cultures as in Example 47. After the 24 hours of growth in stage 2, 5 mg per flask of each of the following mutagens, dissolved in 1.5 mL of DMSO were added to one culture each of *S. griseus* (pH69) and *S. griseus* (pFS) (one culture each of *S. griseus* (pH69) and *S. griseus* (pFS) received only 1.5 mL of DMSO and served as the controls: 2-aminoanthracene (2AA), 1,2-benzanthracene (1,2-BA), and 2,3-benzanthracene (2,3-BA). The resulting cultures were incubated for 24 hours, with shaking. Cells (1 mL) from each culture were harvested, and the bacteria recovered from each were washed three times with 100 mM potassium phosphate buffer, pH 6.7, and resuspended in a small amount of buffer. An aliquot (100 μL) of each of these suspensions was spread on M7Ts plates and incubated for spore formation. After 72 more hours, the spores were harvested and titered on M7Ts and M7Km plates.

Results:

| Strain | Mutagen | Km Titer | Ts Titer | Rev. Freq. | Mut. Ratio |
|---|---|---|---|---|---|
| pH69 | solvent | $1.37 \times 10^2$ | $1.10 \times 10^8$ | $1.24 \times 10^{-6}$ | 1.0 |
| | 2AA | $3.27 \times 10^2$ | $1.20 \times 10^8$ | $2.72 \times 10^{-6}$ | 2.19 |
| | 1,2-BA | $2.33 \times 10^1$ | $1.13 \times 10^8$ | $2.05 \times 10^{-6}$ | 1.65 |
| | 2,3-BA | $3.10 \times 10^2$ | $6.33 \times 10^8$ | $4.89 \times 10^{-7}$ | 0.39 |
| pFS | solvent | $2.00 \times 10^1$ | $5.23 \times 10^8$ | $3.82 \times 10^{-8}$ | 1.0 |
| | 2AA | $4.67 \times 10^1$ | $3.00 \times 10^8$ | $1.56 \times 10^{-7}$ | 4.07 |
| | 1,2-BA | 0.00 | $1.67 \times 10^8$ | — | — |
| | 2,3-BA | $2.33 \times 10^1$ | $1.88 \times 10^9$ | $1.24 \times 10^{-8}$ | 0.32 |

Example 53

This example was done using the protocol of Example 52 and differed only in 1) the testing of different chemicals for mutagenicity and 2) the inclusion of Streptomyces bearing the plasmid HTS1 (HTS1). The chemicals tested were: 9-aminoacridine (9-AAD), 2-nitrofluorene (2-NF), and ICR-191.

Results:

| Strain | Mutagen | Km Titer | Ts Titer | Rev. Freq. | Mut. Ratio |
|---|---|---|---|---|---|
| pH69 | solvent | $5.66 \times 10^2$ | $3.43 \times 10^9$ | $1.65 \times 10^{-7}$ | 1.0 |
| | 9-AAD | $8.66 \times 10^2$ | $2.05 \times 10^9$ | $4.22 \times 10^{-7}$ | 2.56 |
| | 2-NF | $2.87 \times 10^3$ | $4.18 \times 10^9$ | $6.87 \times 10^{-7}$ | 4.16 |
| | ICR-191 | $2.07 \times 10^2$ | $6.83 \times 10^8$ | $3.03 \times 10^{-7}$ | 1.83 |
| pFS | solvent | $2.10 \times 10^2$ | $2.88 \times 10^9$ | $7.29 \times 10^{-8}$ | 1.0 |
| | 9-AAD | $7.40 \times 10^2$ | $7.24 \times 10^9$ | $1.02 \times 10^{-7}$ | 1.40 |
| | 2-NF | $1.10 \times 10^3$ | $9.98 \times 10^9$ | $1.10 \times 10^{-7}$ | 1.51 |
| | ICR-191 | $9.30 \times 10^2$ | $4.25 \times 10^9$ | $2.18 \times 10^{-7}$ | 3.00 |
| pHTS1 | solvent | $2.84 \times 10^9$ | $8.00 \times 10^2$ | $2.82 \times 10^{-7}$ | 1.0 |
| | 9-AAD | $2.93 \times 10^8$ | $6.67 \times 10^1$ | $2.27 \times 10^{-7}$ | 0.80 |
| | 2-NF | $1.05 \times 10^9$ | $2.00 \times 10^1$ | $1.90 \times 10^{-8}$ | 0.07 |
| | ICR-191 | $2.54 \times 10^9$ | $1.00 \times 10^1$ | $3.93 \times 10^{-9}$ | 0.01 |

What is claimed is:

1. A P-450 enzyme product produced by a process for inducing the production of cytochrome P-450 enzyme in bacteria from the genus Streptomyces, the process comprising:

culturing bacteria selected from the group consisting of *Streptomyces griseus* ATCC No. 13273, *Streptomyces griseus* ATCC No. 10137 and *Streptomyces griseus* ATCC No. 55185 in a culture medium comprising at least one inducer selected from the group consisting of soybean flour, genistein and genistin.

2. An enzyme product produced by the process of claim 1 wherein the inducer is genistein.

* * * * *